United States Patent
Koepke et al.

(10) Patent No.: US 9,365,873 B2
(45) Date of Patent: Jun. 14, 2016

(54) GENETICALLY ENGINEERED BACTERIUM WITH ALTERED CARBON MONOXIDE DEHYDROGENASE (CODH) ACTIVITY

(71) Applicants: Michael Koepke, Skokie, IL (US); Fungmin Liew, Nottingham (GB)

(72) Inventors: Michael Koepke, Skokie, IL (US); Fungmin Liew, Nottingham (GB)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 14/753,191

(22) Filed: Jun. 29, 2015

(65) Prior Publication Data

US 2016/0040193 A1  Feb. 11, 2016

Related U.S. Application Data

(60) Provisional application No. 62/036,101, filed on Aug. 11, 2014, provisional application No. 62/036,104, filed on Aug. 11, 2014, provisional application No. 62/036,107, filed on Aug. 11, 2014.

(51) Int. Cl.

| | |
|---|---|
| *C12P 7/02* | (2006.01) |
| *C12P 7/04* | (2006.01) |
| *C12N 9/00* | (2006.01) |
| *C12R 1/145* | (2006.01) |
| *C12P 7/18* | (2006.01) |
| *C12N 15/74* | (2006.01) |
| *C12P 7/06* | (2006.01) |

(52) U.S. Cl.
CPC . *C12P 7/18* (2013.01); *C12N 15/74* (2013.01); *C12P 7/065* (2013.01)

(58) Field of Classification Search
CPC ............. C12P 7/02; C12P 7/06; C12R 1/145; C12N 9/00
See application file for complete search history.

(56) References Cited

U.S. PATENT DOCUMENTS

| | | |
|---|---|---|
| 5,593,886 A | 1/1997 | Gaddy |
| 6,368,819 B1 | 4/2002 | Gaddy et al. |
| 2010/0151543 A1 | 6/2010 | Reeves |
| 2014/0206901 A1 | 7/2014 | Koepke et al. |

FOREIGN PATENT DOCUMENTS

| | | |
|---|---|---|
| KR | 10-2013-0020829 A | 2/2013 |
| KR | 10-2013-0055048 A | 5/2013 |
| WO | 2008028055 A2 | 3/2008 |
| WO | 2009064200 A2 | 5/2009 |

OTHER PUBLICATIONS

Kim, Co-dependent H2 production by genetically engineered Thermococcus onnurineus NA1, Appl Environ Microbiol, 9: 2048-2053, 2013.
International Search Report for International Patent Application PCT/US2015/038395, Korean Intellectual Property Office, Sep. 24, 2015.
Abrini, Arch Microbiol, 161: 345-351, 1994.
Bertram, Arch Microbiol, 151: 551-557, 1989.
Drake, Acetogenic Prokaryotes, In: The Prokaryotes, 3rd edition, p. 354, New York, NY, 2006.
Heap, J Microbiol Meth, 78: 79-85, 2009.
Heap, J Microbiol Meth, 80: 49-55, 2010.
Heap, Nucl Acids Res, 40: e59, 2012.
Köpke, Curr Opin Biotechnol, 22: 320-325, 2011.
Perez, Biotechnol Bioeng, 110:1066-1077, 2012.
Ragsdale, Biochim Biophys Acta, 1784: 1873-1898, 2008.
Ragsdale, J Biol Chem, 258: 2364-2369, 1983.
Tanner, Int J System Bacteriol, 43: 232-236, 1993.
Tirado—Acevedo, Production of bioethanol from synthesis gas using C. ljungdahlii, PhD thesis, North Carolina State University, 2010.

*Primary Examiner* — Maryam Monshipouri
(74) *Attorney, Agent, or Firm* — Andrea E. Schoen

(57) ABSTRACT

The invention provides genetically engineered microorganisms with altered carbon monoxide dehydrogenase (CODH) activity and methods related thereto. In particular, the invention provides a genetically engineered carboxydotrophic acetogenic bacterium having decreased or eliminated activity of CODH1 and/or CODH2. In certain embodiments, the bacterium may also have increased activity of CODH/ACS. The invention further provides a method for producing a product by culturing the bacterium in the presence of a gaseous substrate comprising one or more of carbon monoxide, carbon dioxide, and hydrogen.

19 Claims, 6 Drawing Sheets

(A)

(C)

(B)

GENETICALLY ENGINEERED BACTERIUM WITH ALTERED CARBON MONOXIDE DEHYDROGENASE (CODH) ACTIVITY

CROSS REFERENCE TO RELATED APPLICATIONS

This application claims the benefit of U.S. Provisional Patent Application 62/036,101 filed Aug. 11, 2014, U.S. Provisional Patent Application 62/036,104 filed Aug. 11, 2014, and U.S. Provisional Patent Application 62/036,107 filed Aug. 11, 2014, the entirety of which are incorporated herein by reference.

BACKGROUND OF THE INVENTION

Certain microorganisms can produce fuels, such as ethanol, and other chemicals, such as 2,3-butanediol, by fermentation of gaseous substrates comprising one or more of carbon monoxide (CO), carbon dioxide ($CO_2$), and hydrogen ($H_2$). However, efficient production of such fuels and chemicals may be limited diversion of carbon substrates into undesired byproducts or by slow microorganism growth. Accordingly, there remains a need for genetically engineered microorganisms having improved product and/or growth profiles.

SUMMARY OF THE INVENTION

The invention provides genetically engineered microorganisms with altered carbon monoxide dehydrogenase (CODH) activity and methods related thereto. In particular, the invention provides a genetically engineered carboxydotrophic acetogenic bacterium having decreased or eliminated activity of CODH1 and/or CODH2. The invention further provides a method for producing a product by culturing the bacterium in the presence of a gaseous substrate comprising one or more of CO, $CO_2$, and $H_2$.

The bacterium may be modified to comprise at least one disruptive mutation in a CODH1 gene and/or CODH2 gene, which results in decreased or eliminated activity of CODH1 and/or CODH2. Specifically, the disruptive mutation(s) may reduce or eliminate expression of a CODH1 gene and/or a CODH2 gene. In one embodiment, the disruptive mutation is a knockout mutation.

Furthermore, the bacterium may be modified to have increased activity of CODH/ACS. In one embodiment, the bacterium may overexpresses a CODH/ACS gene, which results in increased activity of CODH/ACS.

The bacterium may produce a number of products or byproducts, including ethanol, 2,3-butanediol, acetate, and/or lactate. In a preferred embodiment, the bacterium produces one or more of ethanol and 2,3-butanediol. The bacterium may also have altered growth characteristics compared to a parental bacterium, such as decreased lag phase or increased growth rate. Preferably, the bacterium produces a higher amount of ethanol, produces a higher amount of 2,3-butanediol, produces a lower amount of acetate, has a shorter lag phase, and/or has a higher growth rate compared to a parental bacterium.

The bacterium generally consumes a gaseous substrate, such as a gaseous substrate comprising one or more of CO, $CO_2$, and $H_2$. The gaseous substrate may be derived from syngas or an industrial process, for example.

In a preferred embodiment, the bacterium is derived from a parental bacterium of *Clostridium autoethanogenum*, *Clostridium ljungdahlii*, or *Clostridium ragsdalei*.

BRIEF DESCRIPTION OF THE DRAWINGS

FIG. 1A shows growth, FIG. 1B shows ethanol production, FIG. 1C shows acetate production, and FIG. 1D shows 2,3-butanediol production. N=3. Error bar=standard error of mean.

FIG. 2A shows growth, FIG. 2B shows ethanol production, and FIG. 2C shows acetate production. N=3. Error bar=standard error of mean.

FIG. 3A shows growth, FIG. 3B shows ethanol production, and FIG. 3C shows acetate production. N=3. Error bar=standard error of mean.

FIG. 5A shows growth, FIG. 5B shows acetate production, FIG. 5C shows ethanol production, FIG. 5C shows ethanol production, FIG. 5D shows 2,3-butanediol production, and FIG. 5E shows lactate production. N=3. Error bar=standard error of mean.

FIG. 6A shows failure of the CODH/ACS-KO mutant to grown on CO. FIG. 6B shows failure of the CODH/ACS-KO mutant to grow on $CO_2+H_2$.

FIG. 7A shows growth, FIG. 7B shows acetate production, FIG. 7C shows ethanol production, and FIG. 7D shows 2,3-butanediol production.

DETAILED DESCRIPTION OF THE INVENTION

Figure 1A:
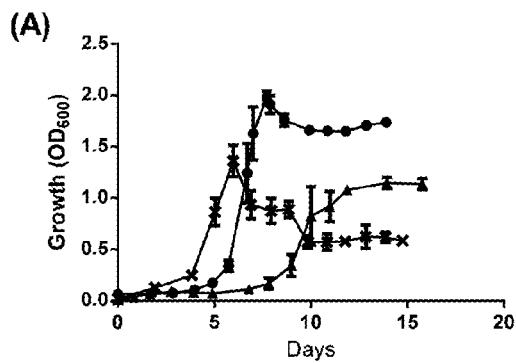
FIGS. 1A-1D are graphs showing growth and metabolite profiles of a CODH1 mutant (triangles), a CODH2 mutant (crosses), and WT *C. autoethanogenum* DSM10061 (circles) on 30 psi CO. In particular.
Figure 1C:
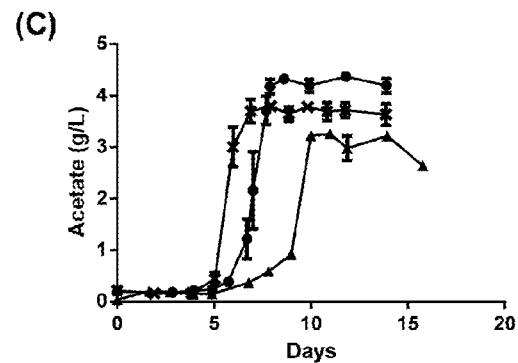

The invention provides, inter alia, novel genetically engineered microorganisms with altered carbon monoxide dehydrogenase (CODH) activity and methods related thereto.

CODH enzymes (EC 1.2.99.2) are oxidoreductases that catalyze the reversible oxidation of CO to $CO_2$ and generate reducing equivalents according to the equation: $CO + H_2O \leftrightarrow CO_2 + 2H^+ + 2e^-$. CODHs are well known in nature and have been described in various organisms, including carboxydotrophic acetogens.

CODHs can be broadly categorized into two classes: (i) the aerobic Cox-type Mo—Cu—Se CODH from carboxydobacteria, which comprises a highly conserved molybdenum active site and uses oxygen (sometimes nitrate) as terminal electron acceptor; and (ii) the anaerobic-type Ni—CODH, which transfer the electrons liberated from CO oxidation to a range of physiological electron acceptors including ferredoxin, cytochromes, flavodoxin, rubredoxin, and NAD(P)+. The reducing equivalents can then be harnessed in several pathways including acetogenesis, methanogenesis, sulphate reduction, hydro genogenesis, and metal reduction.

The $O_2$-sensitive Ni—CODH can be further divided into two groups: (i) Mono-functional CODH which functions physiologically in CO oxidation; and (ii) CODH as part of a bi-functional CODH/ACS complex that couples the reduction of $CO_2$ into CO moiety to acetyl-CoA biosynthesis.

*C. autoethanogenum*, for example, is able to grow autotrophically using CO as the sole source of carbon and energy. Genome sequencing uncovered three putative Ni—CODH in this acetogen: CAETHG_3005 (CODH1), CAETHG_3899 (CODH2), and CAETHG_1620-1621 (AcsA, which encodes the CODH component of the bifunctional CODH/ACS complex). CODH1 is genetically colocalized upstream of a putative 4Fe-4S ferredoxin Fe—S binding protein and ferredoxin-NAD(+) reductase, while CODH2 appears to be an orphan. Similarly, carboxydotrophic acetogens *C. ljungdahlii* and *C. carboxidivorans* are also described to have three CODHs, one bifunctional CODH/ACS and two additional mono-functional CODHs. Additionally, at least CODH1 is found in all sequenced carboxydotrophic acetogens, including *C. ljungdahlii, C. ragsdalei, C. difficile*, and *A. woodii*.

The prior art generally accepts that CODHs, including CODH1 and CODH2, are involved in CO utilization. For example, US 2010/0151543 describes how overexpression of CODH within the acetogenic Clostridia may increase electron flow from syngas components to the oxidized nucleotide cofactors $NAD^+$ and $NADP^+$, whereby the nucleotide cofactors (NADH and NADPH) then stimulate generation of intermediate compounds in Wood-Ljungdahl pathway.

However, the inventors have surprisingly identified that disrupting CODH1 and/or CODH2 in a carboxydotrophic acetogenic microorganism does not negatively affect gas utilization. In fact, the inventors have discovered that disrupting CODH1 and/or CODH2 in a carboxydotrophic acetogenic microorganism results in a microorganism that produces a higher amount of ethanol, produces a lower amount of acetate, has a shorter lag phase, and/or has a higher growth rate compared to an unmodified parental microorganism.

The invention provides a genetically engineered carboxydotrophic acetogenic bacterium having decreased or eliminated activity of CODH1 and/or CODH2. The invention further provides a method for producing a product by culturing the bacterium in the presence of a gaseous substrate comprising one or more of CO, $CO_2$, and $H_2$.

Microorganisms

The microorganism of the invention is genetically engineered, i.e., non-naturally occurring. The term "genetic modification" or "genetic engineering" broadly refers to manipulation of the genome or nucleic acids of a microorganism. Likewise, the term "genetically engineered" refers to a microorganism comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

A "microorganism" is a microscopic organism, especially a bacterium, archaea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. In one embodiment, the parental microorganism is *C. autoethanogenum, C. ljungdahlii*, or *C. ragsdalei*. In a preferred embodiment, the parental microorganism is *C. autoethanogenum* LZ1561, which is deposited under DSMZ accession DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *C. autoethanogenum, C. ljungdahlii*, or *C. ragsdalei*. In a preferred embodiment, the microorganism of the invention is derived from *C. autoethanogenum* LZ1561, which is deposited under DSMZ accession DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a combination thereof. Table 1 provides a representative list of microorganisms and identifies their functional characteristics.

TABLE 1

|  | C1-fixing | Anaerobe | Acetogen | Ethanologen | Autotroph | Carboxydotroph |
|---|---|---|---|---|---|---|
| *Acetobacterium woodii* | + | + | + | +/−[1] | − | +/−[2] |
| *Alkalibaculum bacchii* | + | + | + | + | + | + |
| *Blautia producta* | + | + | + | − | + | + |
| *Butyribacterium methylotrophicum* | + | + | + | + | + | + |
| *Clostridium aceticum* | + | + | + | − | + | + |
| *Clostridium autoethanogenum* | + | + | + | + | + | + |
| *Clostridium carboxidivorans* | + | + | + | + | + | + |
| *Clostridium coskatii* | + | + | + | + | + | + |
| *Clostridium drakei* | + | + | + | − | + | + |
| *Clostridium formicoaceticum* | + | + | + | − | + | + |
| *Clostridium ljungdahlii* | + | + | + | + | + | + |

TABLE 1-continued

| | C1-fixing | Anaerobe | Acetogen | Ethanologen | Autotroph | Carboxydotroph |
|---|---|---|---|---|---|---|
| *Clostridium magnum* | + | + | + | − | + | +/− [3] |
| *Clostridium ragsdalei* | + | + | + | + | + | + |
| *Clostridium scatologenes* | + | + | + | − | + | + |
| *Eubacterium limosum* | + | + | + | − | + | + |
| *Moorella thermautotrophica* | + | + | + | + | + | + |
| *Moorella thermoacetica* (formerly *Clostridium thermoaceticum*) | + | + | + | − [4] | + | + |
| *Oxobacter pfennigii* | + | + | + | − | + | + |
| *Sporomusa ovata* | + | + | + | − | + | +/− [5] |
| *Sporomusa silvacetica* | + | + | + | − | + | +/− [6] |
| *Sporomusa sphaeroides* | + | + | + | − | + | +/− [7] |
| *Thermoanaerobacter kiuvi* | + | + | + | − | + | − |

[1] *Acetobacterium woodi* can produce ethanol from fructose, but not from gas.
[2] It has been reported that *Acetobacterium woodi* can grow on CO, but the methodology is questionable.
[3] It has not been investigated whether *Clostridium magnum* can grow on CO.
[4] One strain of *Moorella thermoacetica*, *Moorella* sp. HUC22-1, has been reported to produce ethanol from gas.
[5] It has not been investigated whether *Sporomusa ovata* can grow on CO.
[6] It has not been investigated whether *Sporomusa silvacetica* can grow on CO.
[7] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, N.Y. 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

More broadly, the microorganism of the invention may be derived from any genus or species identified in Table 1.

In a preferred embodiment, the microorganism of the invention is derived from the cluster of *Clostridia* comprising the species *C. autoethanogenum*, *C. ljungdahlii*, and *C. ragsdalei*. These species were first reported and characterized by Abrini, *Arch Microbiol*, 161: 345-351, 1994 (*C. autoethanogenum*), Tanner, *Int J System Bacteriol*, 43: 232-236, 1993 (*C. ljungdahlii*), and Huhnke, WO 2008/028055 (*C. ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *C. autoethanogenum* from rabbit gut, *C. ljungdahlii* from chicken yard waste, and *C. ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *C. autoethanogenum*, *C. ljungdahlii*, or *C. ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *C. autoethanogenum*, *C. ljungdahlii*, or *C. ragsdalei*. Isolates and mutants of *C. autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *C. ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593, 886), C-01 (ATCC 55988) (U.S. Pat. No. 6,368,819), O-52 (ATCC 55989) (US 6,368,819), and OTA-1 (Tirado-Acevedo, Production of bioethanol from synthesis gas using *C. ljungdahlii*, PhD thesis, North Carolina State University, 2010). Isolates and mutants of *C. ragsdalei* include PI 1 (ATCC BAA-622, ATCC PTA-7826) (WO 2008/028055).

Enzymes

"CODH1" refers to CODH which catalyzes the reversible oxidation of CO to $CO_2$ and generates reducing equivalents according to the equation: $CO+H_2O \leftrightarrow CO_2+2H^++2e^-$. Reference to "CODH1" herein should be taken to include reference to functionally equivalent variants thereof. The CODH1 may be, for example, CODH1 of *C. autoethanogenum* (SEQ ID NO: 1), *C. ragsdalei* (SEQ ID NO: 5), *C. ljungdahlii* (ADK13979.1), *C. difficile* (YP_001086644.1), or *A. woodii* (YP_005269573).

"CODH2" refers to CODH which catalyzes the reversible oxidation of CO to $CO_2$ and generates reducing equivalents according to the equation: $CO+H_2O \leftrightarrow CO_2+2H^++2e^-$. Reference to "CODH2" herein should be taken to include reference to functionally equivalent variants thereof. The CODH2 may be, for example, CODH2 of *C. autoethanogenum* (SEQ ID NO: 3), *C. ragsdalei* (SEQ ID NO: 7), *C. ljungdahlii* (ADK14854.1), *C. scatologenes* (SEQ ID NO: 9), *C. acetobutylicum* (AAK78101.1 and AAK80452.1), *C. carboxidivorans* "P7" (ZP_05390164.1), *C. hydrogenoformans* (ABB14220.1, ABB14432.1 and ABB15066.1), or *C. beijerinckii* (YP_001310115.1). Furthermore, CODH2 homologs can be found in *C. botulinum* (CBO_2218; A5I3Y9), but not in *C. perfringens*, *C. thermocellum*, *C. pasteurianum*, or *C. kluyveri*.

The bifunctional "CODH/ACS" is unique to acetogenic bacteria and, in addition to the reversible oxidation of CO, also catalyzes the synthesis of acetyl-CoA from CO, a methyl group, and CoA. The CODH/ACS enzyme complex consists of multiple subunits: CODH subunit (AcsA); ACS subunit (AcsB); corrinoid iron-sulfur protein large subunit (AcsC); corrinoid iron-sulfur protein small subunit (AcsD); methyltransferase subunit (AcsE); and, CODH accessory protein (CooC). The inventors have discovered that increasing the level of activity of CODH/ACS improves growth and/or product formation. Surprisingly, overexpression of a single CODH subunit of the CODH/ACS complex is sufficient to increase activity of the complex.

The AcsB subunit of CODH/ACS may be, for example, AcsB of *C. autoethanogenum* (CAETHG_1608 gene, WP_023162339.1 protein), *C. ljungdahlii* (CLJU_c37550 gene, WP_013240359.1 protein), *C. ragsdalei* (HQ876032.1 gene, AEI90761.1 protein), *C. carboxidivorans* (Ccar3245 gene, WP_007061841.1), *C. scatalogenes* (WP_029162953.1 protein), *C. difficile* (CD0728 gene, WP_021369307.1 protein), and *A. woodii* (Awo_c10760 gene, WP_014357691.1 protein).

The AcsC subunit of CODH/ACS may be, for example, AcsC of *C. autoethanogenum* (CAETHG_1610 gene, WP_023162341.1 protein), *C. ljungdahlii* (CLJU_c37570 gene, WP_013240361.1 protein), *C. ragsdalei* (HQ876032.1 gene, AEI90763.1 protein), *C. carboxidivorans* (Ccar3247 gene, WP_007061843.1 protein), *C. scatalogenes* (WP_029162955.1 protein), *C. difficile* (CD0730 gene, WP_021369309.1 protein), or *A. woodii* (Awo_c10720 gene, WP_014357687.1 protein).

The AcsD subunit of CODH/ACS may be, for example, AcsD of *C. autoethanogenum* (CAETHG_1611 gene, WP_023162342.1 protein), *C. ljungdahlii* (CLJU_c37580 gene, WP_013240362.1 protein), *C. ragsdalei* (HQ876032.1 gene, AEI90764.1 protein), *C. carboxidivorans* (Ccar3248 gene, WP_007061844.1 protein), *C. scatalogenes* (WP_029162956.1 protein), *C. difficile* (CD0731 gene, WP_021369310.1 protein), or *A. woodii* (Awo_c10710 gene, WP_014357686.1 protein).

The AcsE subunit of CODH/ACS may be, for example, AcsE of *C. autoethanogenum* (CAETHG 1609 gene, WP_023162340.1 protein), *C. ljungdahlii* (CLJU_c37560 gene, WP_013240360.1 protein), *C. ragsdalei* (HQ876032.1 gene, AEI90762.1 protein), *C. carboxidivorans* (Ccar3246 gene, WP 007061842.1 protein), *C. scatalogenes* (WP_029162954.1 protein), *C. difficile* (CD0729 gene, WP_021369308.1 protein), or *A. woodii* (Awo_c10730 gene, WP_014357688.1 protein).

The CooC accessory protein of CODH/ACS may be, for example, CooC of *C. autoethanogenum* (CAETHG_1612 gene, WP_023162343.1 protein), *C. ljungdahlii* (CLJU_c37590 gene, WP_013240363.1 protein), *C. ragsdalei* (HQ876032.1 gene, AEI90765.1 protein), *C. carboxidivorans* (Ccar3249 gene, WP_007061845.1 protein), *C. scatalogenes* (WP_029162957.1 protein), *C. difficile* (CD0732 gene, WP_021369311.1 protein), or *A. woodii* (Awo_c10709 gene, WP_014357685.1 protein).

Sequence information is provided for CODH1, CODH2, and CODH/ACS to identify exemplary sequences applicable to the invention and to allow a skilled person to practice specific embodiments of the invention without undue experimentation. It should be appreciated that nucleic acid and amino acid sequences for CODH1, CODH2, and CODH/ACS may differ from one microorganism to another. Accordingly, the invention should not be construed as being limited to these specific sequences and embodiments, but rather to extend to functionally equivalent variants of any specific CODH1, CODH2, or CODH/ACS referred to herein, including homologs in other strains and species.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *C. acetobutylicum, C. beijerinckii,* or *C. ljungdahlii,* the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art. For example, enzyme assays of use in assessing the activity of CODH1, CODH2, CODH/ACS and variants thereof include anaerobic purification of CODH followed by spectrophotometric measurement of change in absorbance at 604 nm using methyl viologens as electron acceptors (Ragsdale, *J. Biol Chem,* 258: 2364-2369, 1983).

The microorganism of the invention has altered CODH1, CODH2, and/or CODH/ACS activity. "Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" or "reducing" enzyme activity includes decreasing the activity of an enzyme, decreasing the amount of an enzyme, or decreasing the availability of an enzyme to catalyze a reaction. In one embodiment, the function or activity of CODH1 and/or CODH2 is decreased. In another embodiment, the function or activity of CODH1 and/or CODH2 is eliminated or substantially eliminated. In another embodiment, the function or activity of CODH/ACS is increased. In a related embodiment, the function or activity of one or more subunits or accessory proteins of CODH/ACS is increased, particularly the function or activity of the CODH subunit.

As one approach, a change in enzyme activity may be achieved by mutating a gene encoding a protein. "Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation, whereby the gene or protein is made inoperative. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The microorganism of the invention typically comprises at least one disruptive mutation in a CODH1 gene and/or CODH2 gene. Such a mutation may decrease or eliminate expression of the CODH1 gene and/or the CODH2 gene compared to a parental microorganism.

The disruptive mutation may be introduced using any method known in the art. In particular, the disruptive mutation may be introduced by permanently inactivating a gene by targeted insertion of foreign DNA into the coding sequence. A genetic tool known as ClosTron can be used to stably insert an intron (1.8 kb) into a specified locus. Specifically, ClosTron utilizes the specificity of mobile group II intron L1.ltrB from *L. lactis* to propagate into the specified site via a RNA-mediated, retro-homing mechanism (Heap, *J Microbiol Meth,* 80: 49-55, 2010). Another approach involves the transfer of plasmid with homology arms to permanently delete part or whole gene by employing homologous recombination. For instance, a genetic method termed "ACE", or allele-coupled exchange (Heap, *Nucl Acids Res,* 40: e59, 2012) can be used to carry out this deletion without relying on the use of a counter selectable marker.

In some embodiments, the microorganism of the invention has increased activity of CODH/ACS in combination with decreased or eliminated activity of CODH1 and/or CODH2. In particular, the microorganism may overexpress a CODH/ACS gene. Herein, "CODH/ACS gene" refers to any gene encoding any subunit or accessory protein of the CODH/ACS enzyme complex. In a preferred embodiment, the microorganism expresses a gene encoding the CODH subunit of the CODH/ACS enzyme complex. "Overexpressed" refers to an increase in expression of a nucleic acid or protein in the microorganism of the invention compared to the wild-type or parental microorganism from which the microorganism of the invention is derived. Overexpression may be achieved by any means known in the art, including modifying gene copy number, gene transcription rate, gene translation rate, or enzyme degradation rate.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

0060 Nucleic acids of the invention may be codon optimized for expression in a particular strain or species, particularly C. autoethanogenum (including C. autoethanogenum LZ1561), C. ljungdahlii, or C. ragsdalei. "Codon optimization" refers to the mutation of a nucleic acid, such as a gene, for optimized or improved translation of the nucleic acid in a particular strain or species. Codon optimization may result in faster translation rates or higher translation accuracy.

Growth and Products

The microorganism of the invention has an altered growth and/or metabolic profile compared to the parental microorganism from which it is derived. For instance, the microorganism may produce a higher amount of ethanol, produce a higher amount of 2,3-butanediol, produce a lower amount of acetate, have a shorter lag phase, and/or have a higher growth rate compared to the parental microorganism.

The microorganism of the invention may have an altered lag phase. "Lag phase" or "growth lag phase" refers to the amount of time a culture or population of microorganisms takes to reach the early log growth phase or log/exponential growth phase after inoculation. In one embodiment, the microorganism has a shorter lag phase compared to a parental microorganism. For example, the microorganism may have a lag phase that is about 20%, 25%, or 30% shorter than the lag phase of the parental microorganism. In one embodiment, the microorganism has a lag phase that is about 25% to 30% shorter than the lag phase of the parental microorganism. In other embodiments, the microorganism may have a lag phase that is about 3, 5, or 8 times shorter than the lag phase of the parental microorganism. In one embodiment, the lag phase may be about 7.8 to 8 days shorter than the lag phase of the parental microorganism. In another embodiment, the lag phase may be about 1-4 days or less or about 2.9 days or less. In some instances, the microorganism may have a dramatically shorter lag phase than the parental microorganism. For example, the microorganism may have a lag phase that is about 10, 50, 100, or 200 times shorter than the lag phase of the parental microorganism. In one embodiment, the lag phase may be about 0.1 days or less.

The microorganism of the invention may have an altered growth rate. "Growth rate" or "rate of growth" refers to the rate at which a culture or population of microorganisms increases with time. Growth rates are typically expressed herein using the units $h^{-1}$. In one embodiment, the microorganism has an increased or higher growth rate compared to the parental microorganism. For example, the microorganism may have a growth rate that is about 20%, 40%, 60%, 80%, or 100% higher than the growth rate of the parental microorganism. In certain embodiments, the microorganism has a growth rate that is about 2, 3, 4, or 5 times higher than the growth rate of the parental microorganism.

The microorganism of the invention may produce an altered amount of biomass. "Biomass" refers to the collective population of microorganisms generated from a growth or fermentation process. In one embodiment, fermentation of the microorganism produces an increased or higher amount of biomass compared to fermentation of the parental microorganism. For example, fermentation of the microorganism may produce about 20%, 30%, 40%, 50%, 80%, 100%, 120%, 150%, 180%, 200% or 220% more biomass compared to fermentation of the parental microorganism. In one embodiment, fermentation of the microorganism produces about 200% to 220% more biomass compared to fermentation of the parental microorganism.

The microorganism of the invention may produce an altered amount of ethanol. In one embodiment, the microorganism produces an increased or higher amount of ethanol compared to a parental microorganism. For example, the microorganism may produce about 15%, 20%, 30%, 40%, 50%, 60%, 70%, 80%, 90%, 100%, 110%, or 120% more ethanol compared to the parental microorganism. In one embodiment, the microorganism produces about 20% to 113% more ethanol compared to the parental microorganism.

The microorganism of the invention may produce an altered amount of 2,3-butanediol. In one embodiment, the microorganism produces an increased or higher amount of 2,3-butanediol compared to a parental microorganism. For example, the microorganism may produce about 20%, 30%, 40%, 50%, 60%, 70%, 80%, 90%, 100%, 120%, 140%, 160%, 180%, 200%, 220%, 240%, 260%, 270%, 280%, 300%, 320%, or 340% more 2,3-butanediol compared to the parental microorganism. In one embodiment, the microorganism produces about 220% to 230% more 2,3-butanediol compared to the parental microorganism. In another embodiment, the microorganism produces at least about 330% more 2,3-butanediol compared to the parental microorganism. In a further embodiment, the microorganism produces about 300% to 330% more 2,3-butanediol compared to the parental microorganism. In an additional embodiment, the microorganism produces about 0.5-20 g/L 2,3-butanediol.

The microorganism of the invention may produce an altered amount of acetate. The term "acetate" includes both acetate salt alone and a mixture of molecular or free acetic acid and acetate salt. In one embodiment, the microorganism produces a decreased or lower amount of acetate compared to a parental microorganism. For example, the microorganism may produce about 10%, 20%, 30%, 40%, or 50% less acetate compared to the parental microorganism. In one embodiment, the microorganism produces about 18% to 37% less acetate compared to the parental microorganism. In another embodiment, the microorganism produces about 0-5 g/L acetate.

The microorganism of the invention may produce an altered amount of lactate. In one embodiment, the microorganism produces a decreased or lower amount of lactate compared to a parental microorganism.

In a particularly preferred embodiment, the microorganism of the invention produces an increased amount of ethanol and/or 2,3-butanediol and a decreased amount of acetate compared to a parental microorganism.

The microorganism and methods described herein may be used to increase the efficiency of a fermentation process. "Increasing the efficiency," "increased efficiency," and the like include, but are not limited to, increasing microorganism growth rate, product production rate or volume, product volume per volume of substrate consumed, or product selectivity. Efficiency may be measured relative to the performance of a parental microorganism from which the microorganism of the invention is derived.

The microorganism of the invention may also produce one or more additional products. For instance, Clostridium autoethanogenum produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In certain embodiments, microbial biomass itself may be considered a product.

The invention further provides methods for producing one or more products, such as ethanol and/or 2,3-butanediol, by culturing a microorganism of the invention. The invention also provides methods for reducing total atmospheric carbon emissions from an industrial process by using a microorganism of the invention to convert CO, $CO_2$ and/or $H_2$ in an industrial waste gas to useful products.

Substrate

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no $H_2$. $H_2$-rich gas streams may be produced, for example, via steam reformation of hydrocarbons, particularly steam reformation of natural gas, partial oxidation of coal or hydrocarbons, electrolysis of water, and capture byproducts from electrolytic cells used to produce chlorine and from refinery or chemical streams.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no $CO_2$. $CO_2$-rich gas streams include, for example, exhaust gasses from hydrocarbon combustion, such as natural gas or oil combustion, byproducts from the production of ammonia, lime, or phosphate, and natural carbon dioxide wells.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

Effect of Substrate and Genetic Modifications

The composition of the substrate may affect the growth and/or metabolic profile of the microorganism of the invention. For instance, a microorganism grown on CO may have a different growth and/or metabolic profile than a microorganism grown on $CO_2$+$H_2$. Additionally, the particular combination of genetic modifications may affect the growth and/or metabolic profile of the microorganism of the invention. For instance, a microorganism comprising a disruptive mutation in a CODH1 gene may have a different growth and/or metabolic profile than a microorganism comprising a disruptive mutation in a CODH2 gene, which may have a different growth and/or metabolic profile than a microorganism comprising a disruptive mutation in both a CODH1 gene and a CODH2 gene. CODH/ACS overexpression in any of these microorganisms may further alter the growth and/or metabolic profile of the microorganisms. Strategically combining genetic modifications and growing microorganisms on particular substrates may yield growth and/or metabolic profiles tailored to specific applications or production goals.

Growing a CODH1 knockout strain on CO generally results in decreased biomass production, decreased acetate production, increased ethanol production, and similar 2,3-butanediol production. Growing a CODH1 knockout strain on $CO_2$+$H_2$ generally results in a decreased lag phase and faster growth. For example, a CODH1 knockout strain grown on $CO_2$+$H_2$ may have no lag phase and may produce about 0.4 g/L biomass.

Growing a CODH2 knockout strain on CO generally results in decreased lag phase, decreased ethanol production, decreased acetate production, and increased or similar 2,3-butanediol production. For example, a CODH2 knockout strain grown on CO may have a lag phase of 2-4 days and may produce about 0.1-4 g/L acetate. Growing a CODH2 knockout strain on $CO_2$+$H_2$ generally results in decreased lag phase and faster growth. For example, a CODH2 knockout strain grown on $CO_2$+$H_2$ may have a lag phase of 4 days.

Growing a CODH/ACS overexpression strain on CO generally results in decreased lag phase, increased ethanol production, similar acetate production, and increased lactate production.

Fermentation

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

EXAMPLES

The following examples further illustrate the invention but, of course, should not be construed to limit its scope in any way.

Example 1

This example describes group II intron-based insertional inactivation of CODH1 and CODH2 genes involved in carbon fixation in *C. autoethanogenum* DSM10061.

*C. autoethanogenum* DSM10061 was obtained from the DSMZ, the German Collection of Microorganisms and Cell Cultures, Inhoffenstraβe 7B, 38124 Braunschweig, Germany. *E. coli* conjugation strain CA434 was kindly provided by Professor Nigel Minton (University of Nottingham, UK).

The genome of *C. autoethanogenum* DSM10061 encodes the carbon monoxide dehydrogenases (CODHs) CODH1 (SEQ ID NOs: 1 and 2) and CODH2 (SEQ ID NOs: 3 and 4). These CODHs were inactivated using ClosTron group II intron mediated gene disruption tool (Heap, *J Microbiol Meth*, 80: 49-55, 2010). The Perutka algorithm hosted on the ClosTron website was used to identify the group II intron target site between bases 600/601 and 528/529 on the sense strand of the CODH1 and CODH2 genes, respectively. The same algorithm was used to design the intron targeting regions for CODH1 (SEQ ID NO: 15) and CODH2 (SEQ ID NO: 16) which were commercially synthesized by DNA2.0 Inc. (CA) and delivered in pTMLOO7C-E2 vector (HQ263410.1). The final vectors, pMTLOO7C-E2-CODH1-600!601s and pMTLOO7C-E2-CODH2-528!529s contained a retro-transposition-activated ermB marker (RAM) which confered resistance to antibiotic clarithromycin upon insertion into the target site.

The pMTL007C-E2-CODH1-600!601s and pMTL007C-E2-CODH2-528!529s plasmids were introduced into *C. autoethanogenum* DSM10061 as described above and in WO 2012/053905. The transformation mixture was spotted on YTF agar media and incubated at 37° C. inside anaerobic workstation. After 24 hours, the cells were scraped and resuspended in 500 μL PBS and spread on YTF agar media supplemented with 7.5 μg/mL thiamphenicol (Sigma). Transformants were selected using 7.5 μg/mL thiamphenicol. Colonies were observed after 3 days of incubation.

Streaks of single colonies were made sequentially first on YTF media supplemented with 7.5 μg/mL thiamphenicol and 10 μg/mL trimethoprim followed by YTF media containing 6 μg/mL clarithromycin. >8 colonies were randomly screened for group II insertion by PCR (Maxime PCR PreMix kit) using flanking oligonucleotides.

| Primer name | Target gene | WT amplicon size (bp) | Mutant amplicon size (bp) |
|---|---|---|---|
| CODH1-601s-F CODH1-601s-R | CODH1 | 377 | 2177 |
| CODH2-529s-F CODH2-529s-R | CODH2 | 425 | 2225 |
| Univ-0027-F Univ-1492-R | 16s rRNA | 1600 | Not applicable |

Amplification of clarithromycin-resistant colonies using flanking oligonucleotides and gel electrophoresis analysis showed the presence of the larger ClosTron band (>2 kb) instead of the smaller wild-type band (<520 bp), which indicated that the ClosTron group II intron had successfully inserted into the specified CODH sites (CODH1::CTermB-601s and CODH2::CTermB-529s). These amplicons were purified using QIAquick PCR purification kit (Qiagen) and sequence validated by Sanger sequencing (Source Bioscience, UK).

As a final validation step, PCR-verified clones were subjected to Southern blot analysis to confirm single ClosTron insertion. Genomic DNA of the ClosTron mutants were isolated according to Bertram, *Arch Microbiol*, 151: 551-557, 1989 and then digested with restriction enzyme HindIII. Digests were subjected to Southern blot analysis using a random labelled DIG probe (Roche) and was performed according to the manufacturer's instructions. Oligonucleotides EBS2 (SEQ ID NO: 27) and Intron-SalI-R1 (SEQ ID NO: 28) were used to generate the probe, using plasmid pMTL007C-E2 as a template. The resulting probe hybridized to the group II intron. Southern blot analysis detected a single band per mutant clone, indicating single event of group II intron insertion into the genome of *C. autoethanogenum* DSM10061. These validated mutants were termed CODH1::CTermB-601s (or "CODH1 mutant") and CODH2::CTermB-529s (or "CODH2 mutant").

Example 2

This example demonstrates the effect of inactivation of CODH1 in *C. autoethanogenum* DSM10061 cultured under CO conditions.

The ability of CODH1 mutant to grow autotrophically with 100% CO was tested in triplicates of 250 mL serum bottles containing 50 mL PETC media pressurized with 30 psi CO. 0.5 OD600 equivalent of active culture was inoculated into each serum bottle and liquid phase samples were harvested for OD measurements at a wavelength of 600 nm and metabolite analysis by HPLC.

Analysis of metabolites were performed by HPLC using an Agilent 1100 Series HPLC system equipped with a RID operated at 35° C. (Refractive Index Detector) and an Alltech IOA-2000 Organic acid column (150×6.5 mm, particle size 5 µm) kept at 60° C. Slightly acidified water was used (0.005 M $H_2SO_4$) as mobile phase with a flow rate of 0.7 ml/min. To remove proteins and other cell residues, 400 µl samples were mixed with 100 µl of a 2% (w/v) 5-sulfosalicylic acid and centrifuged at 14,000×g for 3 min to separate precipitated residues. 10 µl of the supernatant were then injected into the HPLC for analyses.

As shown in FIGS. 1A-1D, the CODH1 mutant exhibited favorable metabolite profiles in the form of enhanced ethanol at the expense of biomass (42% less) and acetate formation. The CODH1 mutant produced 64% more ethanol (FIG. 1B), 25% less acetate (FIG. 1C), and similar 2,3-butanediol (FIG. 1D) as WT.

Figure 2A:
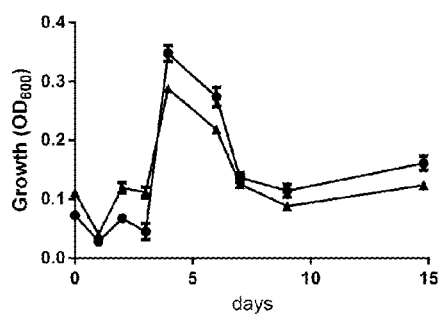
FIGS. 2A-2C are graphs showing growth and metabolite profiles of a CODH1 mutant (triangles) and WT *C. autoethanogenum* DSM10061 (circles) on steel mill gas. In particular.
Figure 2C:
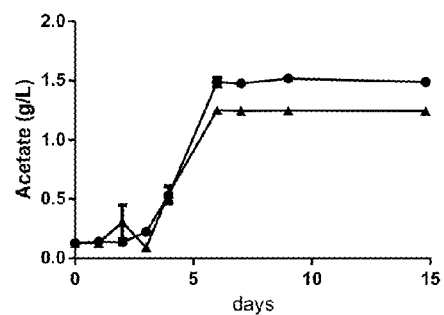
Figure 2B:
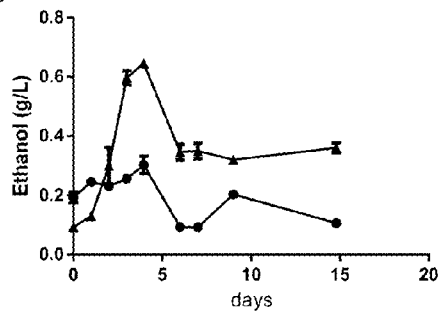

A similar pattern was also observed when the CODH1 mutant and WT were grown in steel mill gas comprising 51.24% CO, 31.22% $N_2$, 11.98% $CO_2$, and 3.05% $H_2$ from a steel mill in Glenbrook, New Zealand. The experiment was conducted in triplicates of 250 mL serum bottles containing 100 mL PETC media and pressurized to 30 psi with steel mill gas. In terms of growth on CO (in steel mill gas), the CODH1 mutant produced 113% more ethanol (FIG. 2B), again at the expense of biomass (17% less) (FIG. 2A) and acetate (18% less) (FIG. 2C) than WT.

Example 3

This example demonstrates the effect of inactivation of CODH2 in *C. autoethanogenum* DSM10061 cultured under CO conditions.

Figure 1B:
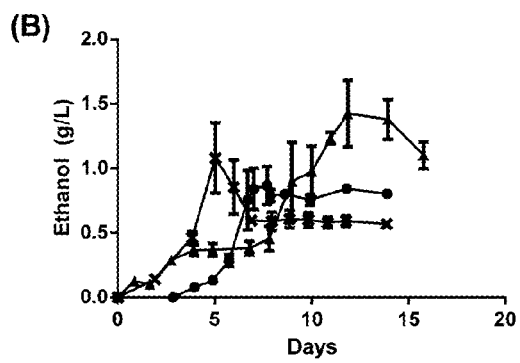
Figure 1D:
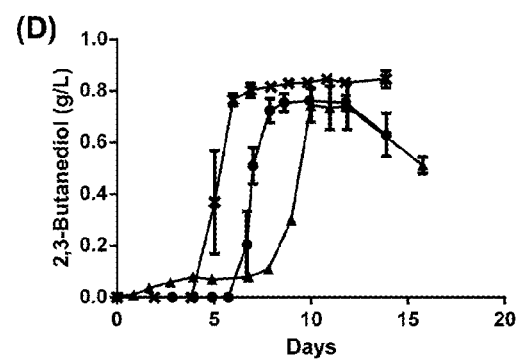

The ability of the CODH2 mutant to grow autotrophically in 100% CO was tested under the same conditions as the CODH1 mutant, described above. In comparison to WT, the CODH2 mutant displayed lag phase reduction of 1 day while utilizing 100% CO as substrate (FIG. 1A). The early exponential phase of the CODH2 mutant occurred at day 3.8, in comparison to exponential phase of WT at day 4.8 (FIG. 1A). The CODH2 mutant produced 27% less acetate (FIG. 1C) and 27% less ethanol than WT (FIG. 1B). However, the peak 2,3-butanediol production of the CODH2 mutant was higher than WT (FIG. 1D).

Example 4

This example demonstrates the effect of inactivation of CODH1 or CODH2 in *C. autoethanogenum* DSM10061 cultured under $H_2+CO_2$ conditions.

To test the ability of the CODH1 and CODH2 mutants to grow in hydrogen and carbon dioxide, WT and the CODH mutants were separately inoculated into 50 mL PETC media (without fructose) in 250 mL serum bottles in triplicates, and the headspace was exchanged with 20 psi $H_2$+10 psi $CO_2$. The cultures were allowed to grow at 37° C. with agitation and samples were harvested for OD600 measurements and HPLC analysis.

Figure 3A:
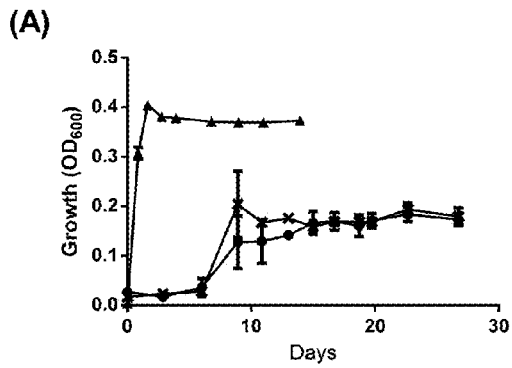
FIGS. 3A-3C are graphs showing growth and metabolite profiles of a CODH1 mutant (triangles), a CODH2 mutant (crosses), and WT *C. autoethanogenum* DSM10061 (circles) under $H_2+CO_2$ conditions. In particular.
Figure 3C:
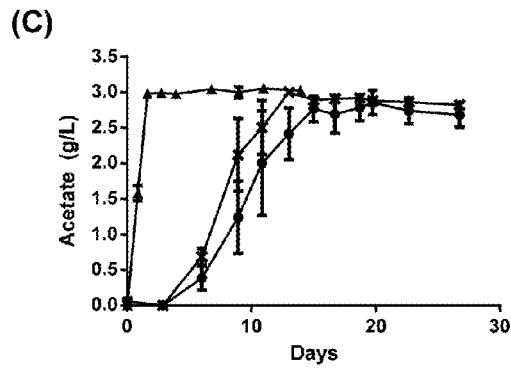
Figure 3B:
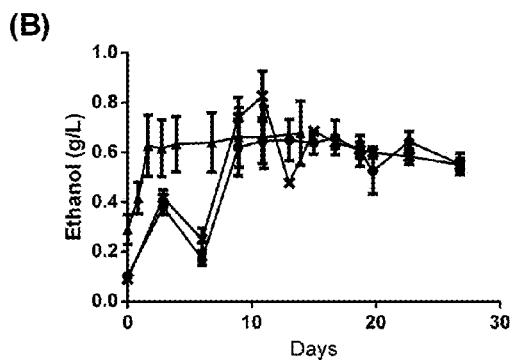
Figure 4:
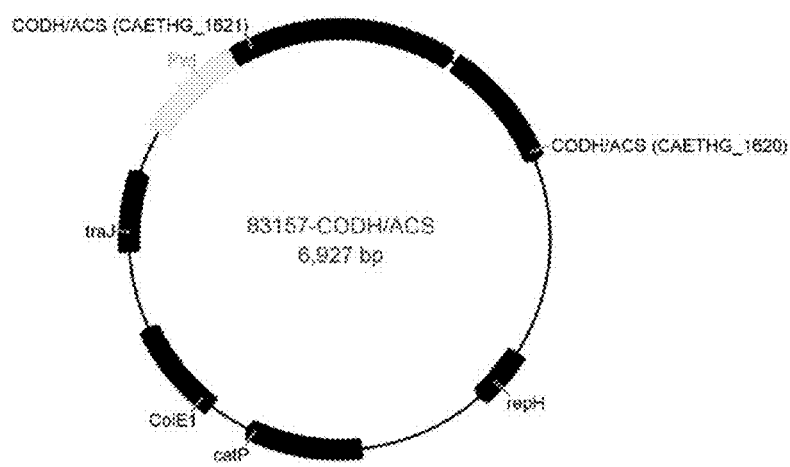
FIG. 4 is a diagram showing a plasmid map of pMTL83157-CODH/ACS.
Figure 5A:
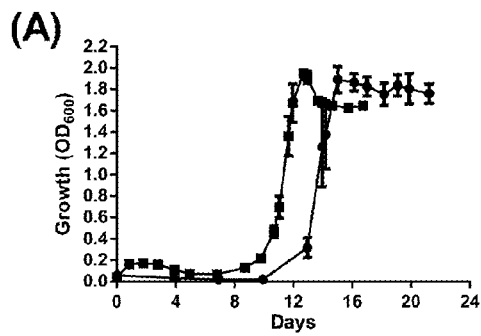
FIGS. 5A-5E are graphs showing the effect of CODH/ACS overexpression on the growth and metabolite profiles of CODH/ACS-overexpressing (pMTL83157-CODH/ACS) (square) and plasmid control pMTL83157 (circle) *C. autoethanogenum* DSM10061 on 100% CO. In particular.
Figure 5B:
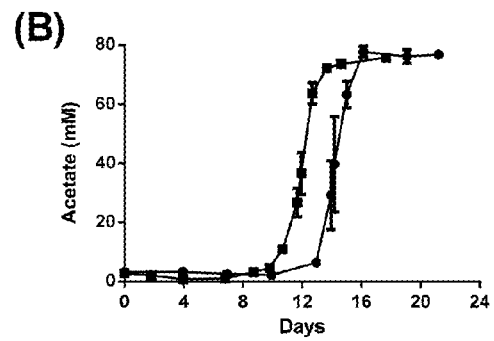
Figure 5C:
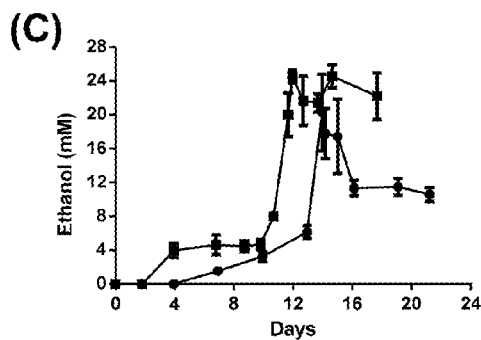
Figure 5D:
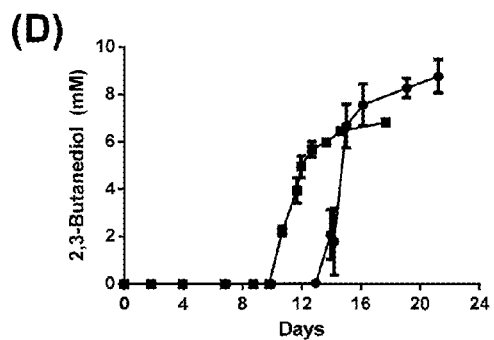
Figure 5E:
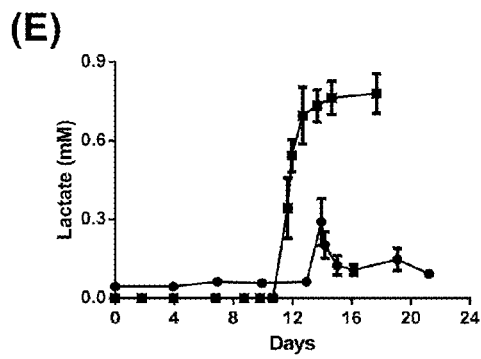

Under $H_2+CO_2$ conditions, the CODH1 mutant displayed a markedly improved growth profile than WT. WT experienced a lag phase of 6 days before reaching a max OD600 of 0.184 on day 22.7, whereas the CODH1 mutant was able to grow without apparent lag phase and reached a max OD600 of 0.40 on day 1.6 (FIG. 3A). The CODH2 mutant displayed a shorter lag phase and faster growth than WT and reached a peak OD600 of 0.20 (FIG. 3A). HPLC analysis showed that very similar levels of acetate and ethanol were produced by the CODH1 mutant, the CODH2 mutant, and WT under $H_2+CO_2$ conditions (FIGS. 3B-5C).

Example 5

This example describes the expected effect of combined inactivation of CODH1 and CODH2 in *C. autoethanogenum* DSM10061 cultured under CO conditions.

Given the desirable metabolite profile of the CODH1 mutant under CO conditions and the reduced lag phase of the CODH1 and CODH2 mutants under both CO and $H_2+CO_2$ conditions, the combined inactivation of CODH1 and CODH2 may result in a strain that has superior growth and metabolite profiles under autotrophic conditions. While not wishing to be bound by any particular theory, inactivation of these two CODHs may increase the availability of CO and/or CO$_2$ for reaction with the CODH/ACS and result in more efficient formation of acetyl-CoA.

For example, allele-coupled exchange or ACE (Heap, *Nucl Acids Res*, 40: e59, 2012) may be used to generate a double CODH (i.e., CODH1 and CODH2) disruption. Using this technique, the pyrE gene (SEQ ID NO: 19) of *C. autoethanogenum* DSM10061 may be deleted so that pyrE can be used as a positive and negative selectable marker for later stages of genetic manipulation. Mutants with deleted pyrE are auxotrophic to uracil auxotrophic and resistant to pro-drug 5'-fluoroorotic acid. As a next step, a ClosTron plasmid targeting one of the CODH may be introduced into pyrE deletion mutant, and clarithromycin resistant colonies may be verified by PCR, sequencing, and Southern Blot. Once ClosTron inactivation of one CODH has been confirmed in this pyrE deletion mutant, an ACE deletion plasmid containing pyrE as a negative selectable marker may be introduced to delete the other CODH. As a final step, an ACE plasmid with the pyrE gene may be introduced to restore pyrE integrity, resulting in a combined CODH1 and CODH2 disruption mutant in a WT background with functional pyrE gene.

Example 6

This example demonstrates the construction and introduction of CODH/ACS overexpression plasmid into *C. autoethanogenum* DSM10061.

*C. autoethanogenum* DSM 10061 was obtained from the DSMZ, the German Collection of Microorganisms and Cell Cultures, InhoffenstraBe 7B, 38124 Braunschweig, Germany. *E. coli* strains DH5α-T1$^R$ and XL1-Blue MRF' were purchased from Invitrogen and Stratagene, respectively.

The DNA sequences of Wood-Ljungdahl promoter (PwL) (SEQ ID NO: 18) and bi-functional carbon monoxide dehydrogenase/acetyl-CoA synthase (CODH/ACS) subunits AcsA (SEQ ID NO: 12) and AcsB (SEQ ID NO: 14), both from *C. autoethanogenum* DSM10061, were obtained from genome sequencing. The Wood-Ljungdahl cluster of *C. autoethanogenum* was found to be highly expressed under autotrophic conditions (Köpke, *Curr Opin Biotechnol*, 22: 320-325, 2011) so P$_{WL}$ was used for expression of CODH/ACS.

Genomic DNA from *C. autoethanogenum* DSM10061 was isolated using a modified method by Bertram, *Arch Microbiol*, 151: 551-557, 1989. A 100 ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 μl lysozyme (~100,000 U) was added and the mixture was incubated at 37° C. for 30 min, followed by addition of 280 μl of a 10% (w/v) SDS solution and another incubation for 10 min. RNA was digested at room temperature by addition of 240 μl of an EDTA solution (0.5 M, pH 8), 20 μl Tris-HCl (1 M, pH 7.5), and 10 μl RNase A (Fermentas). Then, 100 μl Proteinase K (0.5 U) was added and proteolysis took place for 1-3 h at 37° C. Finally, 600 μl of sodium perchlorate (5 M) was added, followed by a phenol-chloroform extraction and an isopropanol precipitation. DNA quantity and quality was inspected spectrophotometrically.

The CODH/ACS gene and P$_{WL}$ were amplified by PCR using Phusion High Fidelity DNA Polymerase (New England Biolabs). The amplified 573 bp P$_{WL}$ was cloned into the *E. coli*-*Clostridium* shuttle vector pMTL 83151 (GenBank accession number FJ797647; Nigel Minton, University of Nottingham; Heap, *J Microbiol Meth*, 78: 79-85, 2009) using NotI and NdeI restriction sites and strain DH5α-T1$^R$ (Invitrogen), resulting in plasmid pMTL83157. Since the coding sequence of CODH/ACS contains one internal NdeI site, splice overlapping (SOE) PCR (Warrens, *Gene*, 186: 29-35, 1997) was used to remove this NdeI site without alteration of the codon. Both the 1946 bp PCR product of CODH/ACS and plasmid pMTL83157 were digested with NdeI and SacI, and ligated to produce plasmid pMTL83157-CODH/ACS (FIG. 4) (SEQ ID NO: 20).

The insert of the expression plasmid pMTL83157-CODH/ACS was completely sequenced using oligonucleotides CODH/ACS-NdeI-F (SEQ ID NO: 31) and CODH/ACS-SacI-R (SEQ ID NO: 32). Sanger sequencing using primers CODH/ACS-NdeI-F and CODH/ACS-SacI-R confirmed that the internal NdeI site of CODH/ACS was successfully altered and free of mutations.

| Target | Oligonucleotide |
|---|---|
| P$_{WL}$ | P$_{WL}$-NotI-F |
| P$_{WL}$ | P$_{WL}$-NdeI-R |
| CODH/ACS | CODH/ACS-NdeI-F |
| CODH/ACS | CODH/ACS-SacI-R |
| CODH/ACS | CODH/ACS-SOE-B |
| CODH/ACS | CODH/ACS-SOE-C |

The plasmids pMTL83157 and pMTL83157-CODH/ACS were introduced into *C. autoethanogenum* DSM10061 by conjugating with donor *E. coli* strain CA434 as donor. Donor strains were grown overnight in LB media supplemented with 25 μg/mL chloramphenicol and 100 μg/mL spectinomycin. Cells from 1.5 mL culture were harvested by centrifugation and washed in phosphate buffered saline (PBS). Inside an anaerobic workstation, the donor cell pellet was resuspended in 200 μL of exponentially growing recipient *C. autoethanogenum* DSM10061. The conjugation mixture was spotted on YTF agar media and incubated at 37° C. inside an anaerobic workstation. After 24 hours, the cells were scrapped and resuspended in 500 μL PBS and spread on YTF agar media supplemented with 7.5 μg/mL thiamphenicol (Sigma) and 10 μg/mL trimethoprim (Sigma). *C. autoethanogenum* transconjugants were selected using 7.5 μg/mL thiamphenicol whereas *E. coli* CA434 strain was counter-selected using 10 μg/mL trimethoprim. Colonies were observed after 3 days of incubation and they were re-streaked onto the same selective agar media for purification.

Likewise, the plasmid could be introduced into other carboxydotrophic acetogens, such as *C. ljungdahlii* or *C. ragsdalei*, using similar protocols.

To check the identity of the transconjugants, the 16s rRNA was amplified and Sanger sequenced using oligonucleotides Univ-0027-F (SEQ ID NO: 25) and Univ-1492-R (SEQ ID NO: 26). Plasmid DNA was extracted from *C. autoethanogenum* transconjugants and transformed into *E. coli* XL1-Blue MRF' (Stratagene) before plasmid restriction digest analysis was carried out. This is commonly referred to as 'plasmid rescue' because plasmids isolated from *Clostridia* are not of sufficient quality for restriction digest analysis. Gel electrophoresis of PmeI and FseI restriction digested plasmids rescued from pMTL83157 transconjugants showed the presence of the expected fragments (2600 bp and 2424 bp). Gel electrophoresis of NdeI and SacI restriction digested plasmids rescued from pMTL83157-CODH/ACS transconjugants showed the presence of the expected fragments (4995 bp and 1932 bp).

Example 7

This example demonstrates the effect of overexpression of CODH/ACS in *C. autoethanogenum* DSM10061 cultured under CO conditions.

The effect of overexpression of CODH/ACS against a plasmid control (pMTL83157) was compared in batch growth experiments with CO as sole carbon and energy source. Under 100% CO, the CODH/ACS overexpression strain showed a reduction in lag phase of growth by 4.2 days, produced 21% more ethanol, and produced 2.7-fold higher lactate titres while generating similar amounts of acetate as the plasmid control (FIGS. 5A-5E).

Both strains were grown autotrophically in 100% CO and were tested in triplicates of 250 mL serum bottles containing 50 mL PETC media and pressurized with 30 psi CO. Thiamphenicol was supplemented to a final concentration 7.5 µg/mL. $OD_{600}$ of 0.5 worth of active culture was inoculated into each serum bottle and liquid phase samples were harvested for OD measurements at a wavelength of 600 nm and metabolite analysis by HPLC.

Analysis of metabolites was performed using Varian ProStar HPLC system equipped with a RID (Refractive Index Detector) operated at 35° C. and a Biorad Aminex HPX-87H column (1300×7.8 mm, particle size 9 µm) kept at 35° C. Slightly acidified water was used (0.005 M $H_2SO_4$) as mobile phase with a flow rate of 0.5 ml/min. To remove proteins and other cell residues, samples were centrifuged at 14000 rpm for 5 minutes and the supernatant was filtered with Spartan 13/0.2 RC filters. 20 µl of the supernatant was then injected into the HPLC for analyses.

Example 8

This example describes the expected effect of overexpression of CODH/ACS in *C. ljungdahlii* cultured under CO conditions.

The CODH/ACS overexpression plasmid described above may also be introduced into *C. ljungdahlii*. *C. ljungdahlii* may be grown on 100% CO. Under these conditions, the CODH/ACS overexpressing *C. ljungdahlii* should show reduced lag phase of growth while improving ethanol and lactate production by at least 20%.

Example 9

This example describes the expected effect of overexpression of CODH/ACS in *C. autoethanogenum* cultured under $CO_2+H_2$ conditions.

The CODH/ACS overexpression strain and plasmid control strain of *C. autoethanogenum* may be grown on PETC-MES media with 80% $CO_2$ and 20% $H_2$ as sole sources of carbon and energy. Under these conditions, the CODH/ACS overexpressing *C. autoethanogenum* should show reduced lag phase of growth and increased ethanol and lactate production by at least 20%.

Example 10

This example demonstrates inactivation of CODH/ACS in *C. autoethanogenum* DSM10061.

The upstream CODH/ACS (CAETHG 1621) of *C. autoethanogenum* DSM10061 was inactivated using ClosTron group II intron mediated gene disruption tool (Heap, *J Microbiol Meth*, 80: 49-55, 2010). The Perutka algorithm hosted at ClosTron website was used to identify the group II intron target site between bases 142/143 on the sense strand of CAETHG_1621. The same algorithm was used to design the intron targeting region (SEQ ID NO: 17) which was commercially synthesized by DNA2.0 Inc. (CA) and delivered in pTML007C-E2 vector (GenBank Accession Number HQ263410.1). The final vector, pMTL007C-E2-CODH/ACS-142!143s, contained a retro-transposition-activated ermB marker (RAM) which conferred resistance to antibiotic clarithromycin upon insertion into the target site.

The pMTL007C-E2-CODH/ACS-142! 143s plasmid was conjugated into *C. autoethanogenum* DSM10061 as described above. *C. autoethanogenum* transconjugants were selected using 7.5 µg/mL thiamphenicol whereas *E. coli* CA434 strain was counter-selected using 10 µg/mL trimethoprim. Colonies were observed after 3 days of incubation. Streaks of single colonies were made sequentially first on YTF media supplemented with 7.5 µg/mL thiamphenicol and 10 µg/mL trimethoprim followed by YTF media containing 6 µg/mL clarithromycin. >8 colonies were randomly screened for group II insertion by PCR (Maxime PCR PreMix kit) using flanking oligonucleotides.

| Primer | Target gene | WT amplicon size (bp) | Mutant amplicon size (bp) |
|---|---|---|---|
| CODHACS-143s-F CODHACS-143s-R | CODH/ACS | 517 | 2317 |

Amplification of clarithromycin resistant colonies using flanking oligonucleotides and gel electrophoresis analysis showed the presence of the larger ClosTron band (>2 kb) instead of the smaller wild-type band (<520 bp), which indicated that the ClosTron group II intron successfully inserted into the specified CODH/ACS site. These amplicons were purified using QIAquick PCR purification kit (Qiagen) and sequence validated by Sanger sequencing (Source Bioscience, UK).

As a final validation step, PCR-verified clones were subjected to Southern blot analysis to confirm single ClosTron insertion. Genomic DNA of the ClosTron mutants were isolated according to Bertram, *Arch Microbiol*, 151: 551-557, 1989 and then digested with restriction enzyme HindIII. Digests were subjected to Southern blot analysis using a random labelled DIG probe (Roche). Oligonucleotides EBS2 (SEQ ID NO: 27) and Intron-SalI-R1 (SEQ ID NO: 28) were used to generate the probe, using plasmid pMTLOO7C-E2 as a template. The resulting probe hybridized to the group II intron. Southern blot analysis detected a single band per mutant clones, indicating single event of group II intron insertion into the genome of *C. autoethanogenum* DSM10061. The validated mutant was termed CODH/ACS::CTermB-143s (or "CODH/ACS KO mutant"). For complementation assay, the overexpression plasmid pMTL83157-CODH/ACS was conjugated into the CODH/ACS KO mutant.

Accordingly, CODH/ACS is required for autotrophic growth (CO or $H_2+CO_2$) of *C. autoethanogenum*.

Example 11

This example demonstrates the effect of inactivation of CODH/ACS in *C. autoethanogenum* DSM10061 grown on fructose.

Figure 6A:
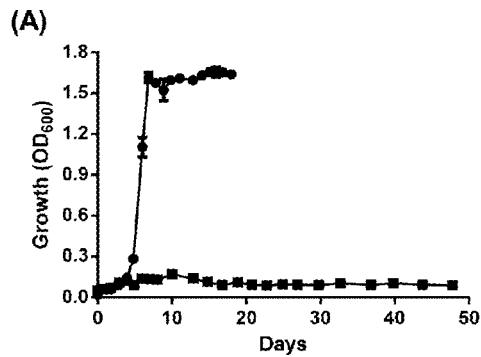
FIGS. 6A-6B are graphs showing the growth of CODH/ACS-inactivated (squares) and WT (circles) *C. autoethanogenum* DSM10061.
Figure 6B:
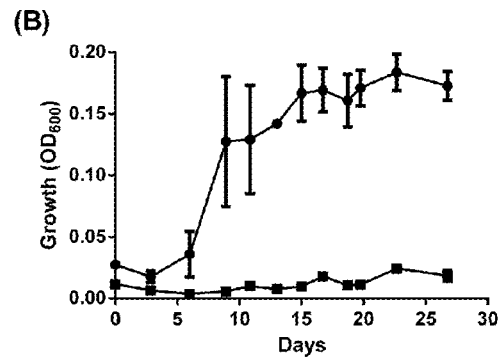

While *C. autoethanogenum* is unable to grow on CO (FIG. 6A) or $CO_2$ and $H_2$ (FIG. 6B) after inactivation of the CODH/ACS enzyme, the strain is still able to grow on sugars, such as fructose. Surprisingly, it was found that under these conditions, the CODH/ACS inactivated strain stops producing acetate. This is especially surprising as acetate formation is typically a hallmark feature of acetogens. During heterotrophic growth, acetogens typically fix $CO_2$ (produced during sugar metabolism) in the presence of $H_2$ into biomass and products via the actions of CODH/ACS and other genes from the Wood-Ljungdahl pathway, also known as the reductive acetyl-CoA pathway.

The CODH/ACS inactivation mutant, the complemented strain, and WT *C. autoethanogenum* DSM10061 were grown in triplicates in 250 mL serum bottles containing 50 mL of PETC media supplemented with 10 g/L fructose (final concentration) under $N_2$ atmosphere. 0.5 $OD_{600}$ equivalent of active culture was inoculated into each serum bottle and liquid phase samples were harvested for OD measurements at a wavelength of 600 nm and metabolite analysis by HPLC.

Figure 7A:
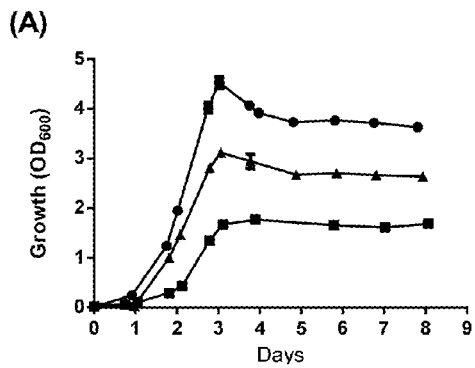
FIGS. 7A-7D are graphs showing the effect of CODH/ACS inactivation on the growth and metabolite profiles of a CODH/ACS KO mutant (squares), a CODH/ACS KO mutant complemented with plasmid pMTL83157-CODH/ACS (triangles), and WT (circles) *C. autoethanogenum* DSM10061 on fructose. In particular.

Inactivation of CODH/ACS significantly reduced peak $OD_{600}$ by 61% from WT level of 4.53 to 1.77 (FIG. 7A). This was also accompanied by an increase in growth lag phase in the CODH/ACS KO mutant (FIG. 7A). The complementation of CODH/ACS activity by plasmid expression of pMTL83157-CODH/ACS in KO mutant increased peak $OD_{600}$ to 3.11 and also shortened the growth lag phase closer to WT level (FIG. 7A).

Figure 7B:
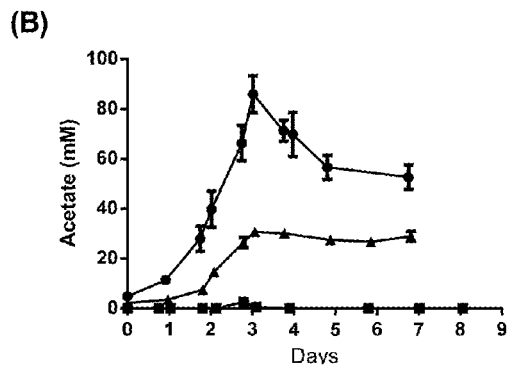

One striking feature of CODH/ACS KO mutant is the lack of acetate production, as only 2.61 mM acetate was momentarily detected on day 2.8 (FIG. 7B). In contrast, the WT produced up to 85.96 mM acetate on day 3.0 (FIG. 7B).

Figure 7C:
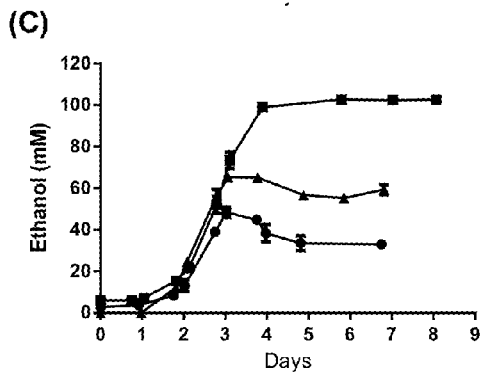
Figure 7D:
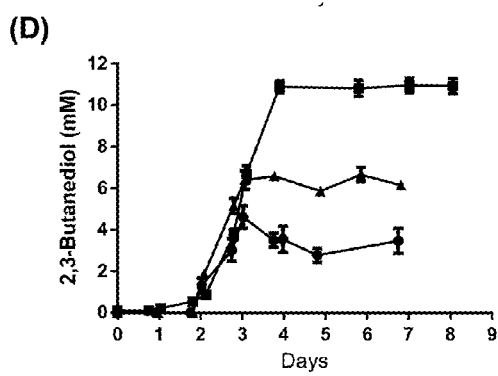

Without significant acetate production, most of the carbon from fructose was diverted towards reduced products ethanol and 2,3-butanediol in the CODH/ACS KO mutant. The inactivation of CODH/ACS increased peak ethanol levels by 113% from WT level of 48.3 mM to 102.7 mM (FIG. 7C). Furthermore, the peak 2,3-butanediol level of the CODH/ACS KO mutant were also 138% higher than WT (10.95 mM vs 4.61 mM) (FIG. 7D). The expression of complementation plasmid pMTL83157-CODH/ACS in the CODH/ACS KO mutant successfully restored acetate, ethanol, and 2,3-butanediol levels closer to WT levels (FIG. 7B-7D), confirming the role of CODH/ACS in *C. autoethanogenum* during heterotrophic growth.

Figure 8:
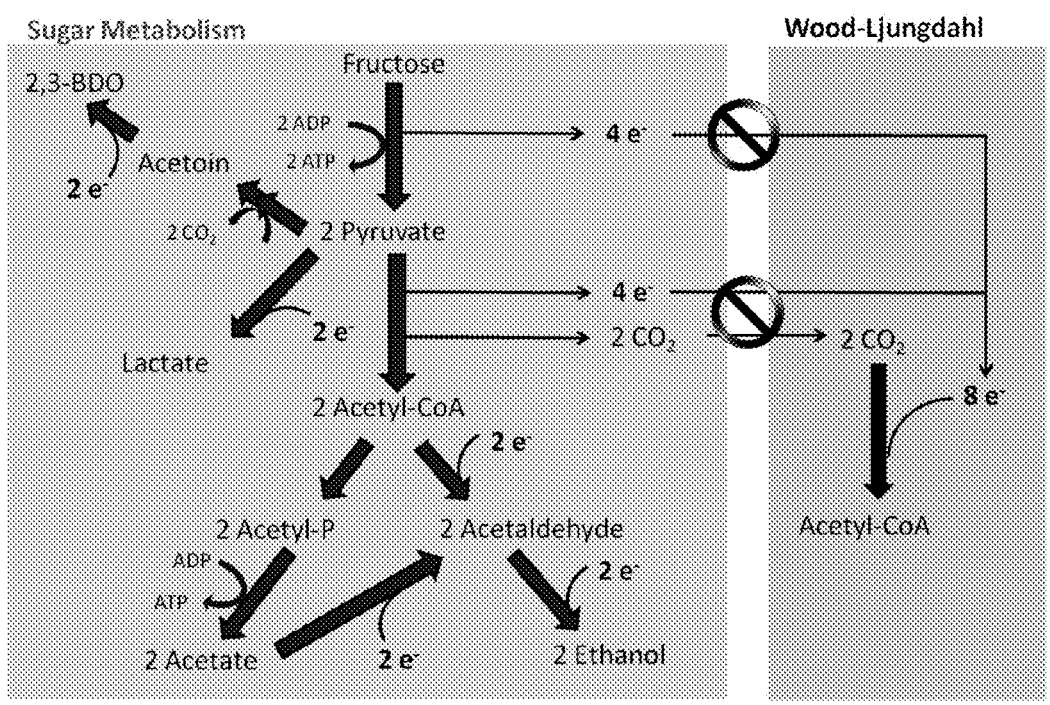
FIG. 8 is a diagram showing that CODH/ACS inactivation may prevent the Wood-Ljungdahl pathway from serving as a sink for reducing equivalents generated during glycolysis so that excessive reducing equivalents generate driving force for ethanol and 2,3-butanediol production.

Without wishing to be bound to any particular theory, it appears that CODH/ACS inactivation prevents the Wood-Ljungdahl pathway from serving as a sink for reducing equivalents generated during glycolysis so that excessive reducing equivalents generate driving force for ethanol and 2,3-butanediol production (FIG. 8).

DESCRIPTION OF THE SEQUENCES

The nucleic acid and amino acid sequences referenced herein are briefly summarized as follows.

| SEQ ID NO: | Sequence type | Description | Species |
|---|---|---|---|
| 1 | amino acid | CODH1 | *Clostridium autoethanogenum* |
| 2 | nucleic acid | CODH1 | *Clostridium autoethanogenum* |
| 3 | amino acid | CODH2 | *Clostridium autoethanogenum* |
| 4 | nucleic acid | CODH2 | *Clostridium autoethanogenum* |
| 5 | amino acid | CODH1 | *Clostridium ragsdalei* |
| 6 | nucleic acid | CODH1 | *Clostridium ragsdalei* |
| 7 | amino acid | CODH2 | *Clostridium ragsdalei* |
| 8 | nucleic acid | CODH2 | *Clostridium ragsdalei* |
| 9 | amino acid | CODH2 | *Clostridium scatologenes* |
| 10 | nucleic acid | CODH2 | *Clostridium scatologenes* |
| 11 | amino acid | AcsA1 | *Clostridium autoethanogenum* |
| 12 | nucleic acid | AcsA1 | *Clostridium autoethanogenum* |
| 13 | amino acid | AcsA2 | *Clostridium autoethanogenum* |
| 14 | nucleic acid | AcsA2 | *Clostridium autoethanogenum* |
| 15 | nucleic acid | Intron targeting region for *Clostridium autoethanogenum* CODH1 | Synthetic |
| 16 | nucleic acid | Intron targeting region for *Clostridium autoethanogenum* CODH2 | Synthetic |
| 17 | nucleic acid | Intron targeting region for *Clostridium autoethanogenum* CODH/ACS | Synthetic |
| 18 | nucleic acid | Promotor region of Wood-Ljungdahl cluster | *Clostridium autoethanogenum* |
| 19 | nucleic acid | pyrE | *Clostridium autoethanogenum* |
| 20 | nucleic acid | pMTL83157-CODH/ACS | Synthetic |
| 21 | nucleic acid | CODH1-601s-F | Synthetic |
| 22 | nucleic acid | CODH1-601s-R | Synthetic |
| 23 | nucleic acid | CODH2-529s-F | Synthetic |
| 24 | nucleic acid | CODH2-529s-R | Synthetic |
| 25 | nucleic acid | Univ-0027-F | Synthetic |
| 26 | nucleic acid | Univ-1492-R | Synthetic |
| 27 | nucleic acid | EBS2 | Synthetic |
| 28 | nucleic acid | Intron-SalI-R1 | Synthetic |
| 29 | nucleic acid | $P_{WL}$-NotI-F | Synthetic |
| 30 | nucleic acid | $P_{WL}$-NdeI-R | Synthetic |
| 31 | nucleic acid | CODH/ACS-NdeI-F | Synthetic |
| 32 | nucleic acid | CODH/ACS-SacI-R | Synthetic |
| 33 | nucleic acid | CODH/ACS-SOE-B | Synthetic |
| 34 | nucleic acid | CODH/ACS-SOE-C | Synthetic |
| 35 | nucleic acid | CODHACS-143s-F | Synthetic |
| 36 | nucleic acid | CODHACS-143s-R | Synthetic |

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A genetically engineered carboxydotrophic acetogenic bacterium having decreased or eliminated activity of CODH1 and/or CODH2 compared to a parental bacterium.

2. The bacterium of claim 1, wherein the bacterium comprises at least one disruptive mutation in a CODH1 gene and/or CODH2 gene.

3. The bacterium of claim 2, wherein the disruptive mutation decreases or eliminates expression of the CODH1 gene and/or the CODH2 gene compared to a parental bacterium.

4. The bacterium of claim 2, wherein the disruptive mutation is a knockout mutation.

5. The bacterium of claim 1, wherein the bacterium additionally has increased activity of CODH/ACS compared to the parental bacterium.

6. The bacterium of claim 5, wherein the bacterium overexpresses a CODH/ACS gene compared to the parental bacterium.

7. The bacterium of claim 1, wherein the bacterium produces one or more of ethanol and 2,3-butanediol.

8. The bacterium of claim 1, wherein the bacterium produces a higher amount of ethanol, produces a lower amount of acetate, has a shorter lag phase, and/or has a higher growth rate compared to the parental bacterium.

9. The bacterium of claim 1, wherein the bacterium consumes a gaseous substrate comprising one or more of CO, $CO_2$, and $H_2$.

10. The bacterium of claim 1, wherein the parental bacterium is *Clostridium autoethanogenum*, *Clostridium ljungdahlii*, or *Clostridium ragsdalei*.

11. A method for producing a product, comprising culturing the bacterium of claim 1 in the presence of a gaseous substrate comprising one or more of CO, $CO_2$, and $H_2$, whereby the bacterium produces a product.

12. The method of claim 11, wherein the bacterium comprises at least one disruptive mutation in a CODH1 gene and/or CODH2 gene.

13. The method of claim 12, wherein the disruptive mutation decreased or eliminates expression of the CODH1 gene and/or the CODH2 gene compared to a parental bacterium.

14. The method of claim 12, wherein the disruptive mutation is a knockout mutation.

15. The method of claim 11, wherein the bacterium additionally has increased activity of CODH/ACS compared to the parental bacterium.

16. The method of claim 15, wherein the bacterium overexpresses a CODH/ACS gene compared to the parental bacterium.

17. The method of claim 11, wherein the product comprises one or more of ethanol and 2,3-butanediol.

18. The method of claim 11, wherein the bacterium produces a higher amount of ethanol, produces a lower amount of acetate, has a shorter lag phase, and/or has a higher growth rate compared to the parental bacterium.

19. The method of claim 11, wherein the parental bacterium is *Clostridium autoethanogenum*, *Clostridium ljungdahlii*, or *Clostridium ragsdalei*.

* * * * *

```
                              SEQUENCE LISTING

<160> NUMBER OF SEQ ID NOS: 36

<210> SEQ ID NO 1
<211> LENGTH: 626
<212> TYPE: PRT
<213> ORGANISM: Clostridium autoethanogenum

<400> SEQUENCE: 1

Met Ser Asn Asn Lys Ile Cys Lys Ser Ala Asp Lys Val Leu Glu Lys
1               5                   10                  15

Phe Ile Gly Ser Leu Asp Gly Val Glu Thr Ser His His Arg Val Glu
                20                  25                  30

Ser Gln Ser Val Lys Cys Gly Phe Gly Gln Leu Gly Val Cys Cys Arg
            35                  40                  45

Leu Cys Ala Asn Gly Pro Cys Arg Ile Thr Pro Lys Ala Pro Arg Gly
        50                  55                  60

Val Cys Gly Ala Ser Ala Asp Thr Met Val Ala Arg Asn Phe Leu Arg
65                  70                  75                  80

Ala Val Ala Ala Gly Ser Gly Cys Tyr Ile His Ile Val Glu Asn Thr
                85                  90                  95

Ala Arg Asn Val Lys Ser Ile Gly Glu Thr Gly Gly Glu Ile Lys Gly
            100                 105                 110

Met Asn Ala Leu Asn Thr Leu Ala Glu Lys Leu Gly Ile Thr Glu Ser
        115                 120                 125

Asp Pro His Lys Lys Ala Val Leu Val Ala Asp Ala Val Leu Lys Asp
    130                 135                 140

Leu Tyr Lys Pro Lys Phe Glu Lys Met Glu Val Ile Asn Lys Leu Ala
145                 150                 155                 160

Tyr Ala Pro Arg Leu Glu Asn Trp Asn Lys Leu Asn Ile Met Pro Gly
                165                 170                 175

Gly Ala Lys Ser Glu Val Phe Asp Gly Val Val Lys Thr Ser Thr Asn
            180                 185                 190

Leu Asn Ser Asp Pro Val Asp Met Leu Leu Asn Cys Leu Lys Leu Gly
        195                 200                 205

Ile Ser Thr Gly Ile Tyr Gly Leu Thr Leu Thr Asn Leu Leu Asn Asp
    210                 215                 220

Ile Val Leu Gly Glu Pro Ala Ile Arg Pro Ala Lys Val Gly Phe Lys
```

```
            225                 230                 235                 240
   Val Val Asp Thr Asp Tyr Ile Asn Leu Met Ile Thr Gly His Gln His
                       245                 250                 255

Ser Met Ile Ala His Leu Gln Glu Glu Leu Val Lys Pro Glu Ala Val
                       260                 265                 270

Lys Lys Ala Gln Ala Val Gly Ala Lys Gly Phe Lys Leu Val Gly Cys
                       275                 280                 285

Thr Cys Val Gly Gln Asp Leu Gln Leu Arg Gly Lys Tyr Tyr Thr Asp
                       290                 295                 300

Val Phe Ser Gly His Ala Gly Asn Asn Phe Thr Ser Glu Ala Leu Ile
   305                 310                 315                 320

Ala Thr Gly Gly Ile Asp Ala Ile Val Ser Glu Phe Asn Cys Thr Leu
                       325                 330                 335

Pro Gly Ile Glu Pro Ile Ala Asp Lys Phe Met Val Lys Met Ile Cys
                       340                 345                 350

Leu Asp Asp Val Ser Lys Lys Ser Asn Ala Glu Tyr Val Glu Tyr Ser
                       355                 360                 365

Phe Lys Asp Arg Glu Lys Ile Ser Asn His Val Ile Asp Thr Ala Ile
                       370                 375                 380

Glu Ser Tyr Lys Asn Arg Arg Ser Lys Val Thr Met Asn Ile Pro Lys
   385                 390                 395                 400

Asn His Gly Phe Asp Asp Val Ile Thr Gly Val Ser Glu Gly Ser Leu
                       405                 410                 415

Lys Ser Phe Leu Gly Gly Ser Trp Lys Pro Leu Val Asp Leu Ile Ala
                       420                 425                 430

Ala Gly Lys Ile Lys Gly Val Ala Gly Ile Val Gly Cys Ser Asn Leu
                       435                 440                 445

Thr Ala Lys Gly His Asp Val Phe Thr Val Glu Leu Thr Lys Glu Leu
                       450                 455                 460

Ile Lys Arg Asn Ile Ile Val Leu Ser Ala Gly Cys Ser Ser Gly Gly
   465                 470                 475                 480

Leu Glu Asn Val Gly Leu Met Ser Pro Gly Ala Ala Glu Leu Ala Gly
                       485                 490                 495

Asp Ser Leu Lys Glu Val Cys Lys Ser Leu Gly Ile Pro Pro Val Leu
                       500                 505                 510

Asn Phe Gly Pro Cys Leu Ala Ile Gly Arg Leu Glu Ile Val Ala Lys
                       515                 520                 525

Glu Leu Ala Glu Tyr Leu Lys Ile Asp Ile Pro Gln Leu Pro Leu Val
                       530                 535                 540

Leu Ser Ala Pro Gln Trp Leu Glu Glu Gln Ala Leu Ala Asp Gly Ser
   545                 550                 555                 560

Phe Gly Leu Ala Leu Gly Leu Pro Leu His Leu Ala Ile Ser Pro Phe
                       565                 570                 575

Ile Gly Gly Ser Lys Val Val Thr Lys Val Leu Cys Glu Asp Met Glu
                       580                 585                 590

Asn Leu Thr Gly Gly Lys Leu Ile Ile Glu Asp Asp Ile Ile Lys Ala
                       595                 600                 605

Ala Asp Lys Leu Glu Glu Thr Ile Leu Ala Arg Arg Lys Ser Leu Gly
                       610                 615                 620

Leu Asn
   625

<210> SEQ ID NO 2
```

<211> LENGTH: 1881
<212> TYPE: DNA
<213> ORGANISM: Clostridium autoethanogenum

<400> SEQUENCE: 2

```
atgtcaaata caaaatttg taaatcagca gataaggtac ttgaaaagtt tataggttct      60
ctagatggtg tagaaacttc tcatcatagg gtagaaagcc aaagtgttaa atgtggtttt    120
ggtcagctag gagtctgctg tagactctgt gcaaacggtc cctgtaggat aacacctaaa    180
gctccaagag gagtatgtgg tgctagtgct gataccatgg ttgcaagaaa ctttcttaga    240
gctgtagctg ccggcagtgg atgttatatt catatagtcg aaaatacagc tagaaacgta    300
aaatccatag gtgaaaccgg cggcgagata aaggaatga atgctctcaa tacactggca    360
gaaaaattag gtataacaga atctgaccca cataaaaaag ctgtactagt agctgatgcc    420
gtattaaagg acttatacaa accaaaattt gaaaaaatgg aagttataaa taaattagct    480
tatgcaccta gactagaaaa ttggaacaaa ttaaatataa tgcctggcgg tgcaaaatca    540
gaagttttg atggtgtagt aaaaacttct acaaatctaa acagtgaccc tgtagatatg    600
cttctaaatt gtttaaaact tggaatatcc actggaattt atggacttac ccttacaaat    660
ttattaaatg acatagtttt aggtgaacct gctataagac ctgcaaaagt tggttttaaa    720
gttgtagata cggattatat aaatttgatg ataacaggcc accagcactc catgattgcc    780
catcttcaag aagaacttgt aaaacctgaa gctgtaaaaa aggcccaagc agttggtgct    840
aaaggattca aactagttgg atgtacctgt gtaggacagg atttacagtt aagaggtaaa    900
tactatactg atgttttctc cggccatgca ggaaataatt ttacaagtga agccttaata    960
gcaactggag gtatagatgc aatagtatct gaattcaact gtactcttcc tggcatcgag   1020
ccaatagctg ataagttcat ggttaaaatg atatgcctag atgacgtttc taaaaaatca   1080
aatgcagaat atgtagaata ttcctttaaa gatagagaaa aataagcaa ccatgttata   1140
gatacagcta ttgaaagcta taagaacaga agatctaaag ttacaatgaa tattcctaaa   1200
aaccatggct ttgatgacgt cataacaggt gtaagtgaag gttccttaaa atctttctta   1260
ggtggcagct ggaaacctct agtagactta attgctgctg gaaaaattaa aggtgttgct   1320
ggaatagtag gttgttcaaa cttaactgcc aaaggtcatg atgtatttac agtagaactt   1380
acaaaagaac ttataaagag aaatataatt gtgctttctg caggttgttc aagtggtgga   1440
cttgaaaatg taggacttat gtctccagga gctgctgaac ttgcaggaga tagcttaaaa   1500
gaagtatgta agagcctagg aataccacct gtactaaatt ttggtccatg tcttgctatt   1560
ggaagattgg aaattgtagc aaaagaacta gcagaatatc taaaaataga tattccacag   1620
cttccacttg tactttctgc acctcaatgg cttgaagaac aagcattagc agatggaagt   1680
tttggtcttg ccccttggatt accacttcac cttgctatat ctcctttat tggtggaagt   1740
aaagtggtaa caaagttttt atgtgaagac atggaaaatc taacaggcgg caagcttata   1800
atagaagacg atataataaa agctgcagat aaattagaag aaaccatact tgcaagaagg   1860
aaaagcttag gtcttaatta a                                              1881
```

<210> SEQ ID NO 3
<211> LENGTH: 643
<212> TYPE: PRT
<213> ORGANISM: Clostridium autoethanogenum

<400> SEQUENCE: 3

Met Ser Gln Thr Thr Leu Glu Lys Asn Glu Thr Ile Arg Glu Arg Thr

```
1               5                   10                  15
Glu Gly Arg Val Ser Tyr His Asp Ser Val Glu Glu Met Leu Lys Arg
                20                  25                  30

Ile Arg Glu Asp Gly Met Ser Asn Val Phe Asp Arg Trp Ser Ser Gln
                35                  40                  45

Glu Lys Ile Arg Cys Lys Phe Cys Leu Gly Leu Ser Cys Gln Leu
    50                  55                  60

Cys Ser Gln Gly Pro Cys Arg Ile Asn Leu Lys Gly Glu Gln Lys Lys
65                  70                  75                  80

Gly Val Cys Gly Ile Gly Pro Asp Ala Met Ala Met Arg Asn Met Leu
                85                  90                  95

Leu Lys Asn Ile Met Gly Ala Gly Thr Tyr Ser His His Ala Tyr Glu
                100                 105                 110

Ala Phe Arg Thr Leu Arg Glu Thr Gly Glu Gly Lys Thr Pro Phe Thr
                115                 120                 125

Ile Lys Asp Leu Asp Lys Leu Lys Trp Met Cys Gln Lys Val Gly Ile
                130                 135                 140

Asp Thr Ser Gly Asp Thr Asn Lys Met Ala Val Asp Leu Ala Asn Phe
145                 150                 155                 160

Leu Glu Ala Glu Met Gly Lys Asp Val Glu Pro Ser Val Met Val
                165                 170                 175

Asp Val Phe Ser Pro Arg Lys Arg Lys Val Trp Lys Asp Leu Gly
                180                 185                 190

Ile Tyr Pro Ser Gly Val Val His Glu Glu Gln Asn Ala Val Ala Ser
                195                 200                 205

Cys Leu Thr Asn Val Asp Gly Asp Tyr Val Ser Leu Ala Lys Lys Ala
210                 215                 220

Leu Arg Leu Gly Leu Ser Thr Ile Tyr Thr Ala Gln Ile Gly Leu Glu
225                 230                 235                 240

Met Val Gln Asp Ile Leu Phe Gly Thr Pro Thr Pro His Glu Val Asn
                245                 250                 255

Val Asp Leu Gly Ile Met Asp Pro Glu Tyr Ile Asn Ile Val Phe Asn
                260                 265                 270

Gly His Gln Pro Trp Ala Gly Val Ala Thr Ile Gln Lys Ala Lys Met
                275                 280                 285

Gln Gln Ile Gln Glu Arg Ala Lys Ala Val Gly Ala Lys Gly Leu Arg
                290                 295                 300

Ile Val Gly Ser Ile Glu Thr Gly Gln Glu Leu Leu Gln Arg Phe Glu
305                 310                 315                 320

Val Asp Asp Val Phe Val Gly Leu Met Gly Asp Trp Leu Ser Ile Glu
                325                 330                 335

Pro Leu Leu Ala Thr Gly Thr Val Asp Val Leu Ala Met Glu Glu Asn
                340                 345                 350

Cys Ser Pro Pro Ala Ile Asp His Tyr Ala Glu Lys Tyr Gln Val Thr
                355                 360                 365

Leu Val Gly Val Ser Thr Ile Ile Gly Ile Pro Gly Leu Asn His Met
                370                 375                 380

Ile Pro Tyr Asn Pro Glu Lys Val Gly Glu Met Ala Asp Lys Leu Ile
385                 390                 395                 400

Asp Leu Ala Ile Glu Asn Phe Lys Lys Arg Lys Asp Asn Ile Thr Pro
                405                 410                 415

Lys Val Pro Lys Ile Thr Gln Lys Ala Ile Ala Gly Phe Ser Thr Glu
                420                 425                 430
```

```
Ala Val Leu Lys Ala Leu Gly Asn Lys Leu Asp Pro Leu Asp Val
        435                 440                 445
Ile Lys Ala Gly Lys Ile Lys Gly Ile Val Ala Leu Ala Asn Cys Ser
    450                 455                 460
Thr Leu Arg Asn Gly Pro Gln Asp Trp Asn Thr Val Asn Leu Val Lys
465                 470                 475                 480
Glu Leu Ile Lys Lys Asp Ile Leu Val Val Ala Gly Gly Cys Gly Asn
                485                 490                 495
His Ala Leu Glu Val Ala Gly Leu Cys Asn Leu Asp Ala Ile Asn Met
            500                 505                 510
Ala Gly Gln Gly Leu Glu Glu Val Cys Asn Met Leu Lys Ile Pro Pro
        515                 520                 525
Val Leu Ser Phe Gly Thr Cys Thr Asp Thr Gly Arg Ile Ser Met Leu
    530                 535                 540
Val Thr Glu Leu Ala Asn His Leu Asp Val Asp Ile Pro Asp Leu Pro
545                 550                 555                 560
Ile Ala Val Thr Ala Pro Glu Trp Met Glu Gln Lys Ala Thr Ile Asp
                565                 570                 575
Gly Leu Phe Ala Val Ala Tyr Gly Ala Tyr Thr His Leu Ser Pro Thr
            580                 585                 590
Pro Phe Leu Thr Gly Ala Glu Gln Leu Val Lys Leu Leu Thr Glu Asp
        595                 600                 605
Val Glu Asn Leu Thr Gly Gly Lys Val Ala Leu Gly Asp Asn Pro Lys
    610                 615                 620
Glu Ala Ala Asp Asn Ile Glu Ala His Ile Leu Ser Lys Arg Glu Gly
625                 630                 635                 640

Leu Gly Leu

<210> SEQ ID NO 4
<211> LENGTH: 1932
<212> TYPE: DNA
<213> ORGANISM: Clostridium autoethanogenum

<400> SEQUENCE: 4
atgagtcaaa ctacactaga aaaaaatgaa actatacgag aaagaacaga agggcgagtt      60
agctatcacg attctgtaga ggaaatgctt aaaagaatca gagaagatgg tatgtcaaat     120
gtatttgaca gatggtcctc tcaagaaaaa attagatgta agttttgcct agaaggattg     180
agctgtcaat tgtgttctca aggcccctgc agaattaatc ttaaaggaga cagaaaaaa      240 ggtgtttgtg gaattggccc agatgctatg gcaatgcgaa atatgttact taaaaacata     300
atgggagctg gtacatatag ccatcatgca tatgaagcct ttagaacatt aagagaaact     360
ggggaaggca agactccatt tacaattaaa gacttggata aactcaaatg gatgtgccag     420
aaagttggaa ttgatacaag tggagatact aataaaatgg cagtggatct ggcaaacttt     480
ttggaagctg aaatgggtaa agatgtagag gaacccagtg ttatggtaga gtgtgttttca     540 ccaaggaaga gaaaaaaagt ttggaaagat cttggaattt atccttcagg agtagttcac     600
gaagagcaaa atgcagtagc aagttgctta acaaatgttg atggagatta tgtatcatta     660
gctaaaaaag cgctgcggtt aggcctatca actatttata cagcacaaat aggacttgaa     720
atggtacagg atatactttt tggcacgcct acaccccatg aggtaaatgt ggacttagga     780
attatggatc cagagtatat aaatattgta tttaatggac atcaaccttg gctggtgtt      840 gctaccattc aaaaggcaaa gatgcagcag atacaggaaa gagcaaaggc agttggtgca     900
```

```
aaagggctta gaatagttgg gtcaattgaa acagggcagg agctattaca aagatttgaa    960
gtagatgatg tatttgtagg tttaatggga gattggctat ctatagaacc acttcttgct   1020
acaggtacag ttgatgttct tgcaatggaa gaaaactgtt ctccacctgc aatagatcat   1080
tatgctgaaa agtatcaggt aactttagta ggggtaagta ctattatagg tattccggga   1140
ttaaatcata tgattccata taatcctgaa aaagtgggtg aaatggctga caaattgatt   1200
gatttggcca ttgaaaattt taaaaagaga aaggataaca ttacaccaaa ggttcctaaa   1260
ataacacaga aagcaatagc aggtttttct actgaagcag ttttaaaagc tttaggaaat   1320
aagcttgatc cacttgttga tgttattaag gcaggaaaga ttaaaggaat tgtggctttg   1380
gcaaattgtt caactctaag aaatggtcct caagattgga atacagttaa tctggtaaag   1440
gaattgatta aaaaggatat tttagttgtg ctggtgggt gcggcaatca tgctcttgaa    1500
gtagcagggc tgtgcaacct agatgcaata acatggctg gccaaggatt agaagaagta    1560
tgcaatatgc taaagattcc tccagttcta agctttggaa cttgtacaga tacgggaaga   1620
atatccatgc ttgttacaga acttgctaat caccttgatg tagatatacc agatcttcct   1680
attgcagtaa cggcccccga gtggatgaaa caaaaagcta ctatagatgg tttatttgca   1740
gtagcctatg gggcatatac acatttatct ccgaccccat ttctaacagg tgcagaacag   1800
cttgtaaagc ttcttactga ggatgtgag aatttaacag gaggtaaagt tgcattagga    1860
gacaatccca aagaggcagc tgataatatt gaagcacata tattaagtaa aagagagggt   1920
ttggggttat aa                                                       1932
```

<210> SEQ ID NO 5
<211> LENGTH: 633
<212> TYPE: PRT
<213> ORGANISM: Clostridium ragsdalei

<400> SEQUENCE: 5

```
Met Ser Asn Asn Lys Ile Cys Lys Ser Ala Asp Lys Val Leu Glu Lys
1               5                   10                  15

Phe Ile Gly Ser Leu Asp Gly Val Glu Thr Ser His His Arg Val Glu
            20                  25                  30

Ser Gln Ser Val Lys Cys Gly Phe Gly Gln Leu Gly Val Cys Cys Arg
        35                  40                  45

Leu Cys Ala Asn Gly Pro Cys Arg Ile Thr Pro Lys Ala Pro Arg Gly
    50                  55                  60

Val Cys Gly Ala Ser Ala Asp Thr Met Val Ala Arg Asn Phe Leu Arg
65                  70                  75                  80

Ala Val Ala Ala Gly Ser Gly Cys Tyr Ile His Ile Val Glu Asn Thr
                85                  90                  95

Ala Arg Asn Val Lys Ser Val Gly Glu Thr Gly Gly Glu Ile Lys Gly
            100                 105                 110

Met Asn Ala Leu Asn Thr Leu Ala Glu Lys Leu Gly Ile Thr Glu Ser
        115                 120                 125

Asp Pro His Lys Lys Ala Val Leu Val Ala Asp Ala Val Leu Lys Asp
    130                 135                 140

Leu Tyr Lys Pro Lys Phe Glu Lys Met Glu Val Ile Asn Lys Leu Ala
145                 150                 155                 160

Tyr Ala Pro Arg Leu Glu Asn Trp Asn Lys Leu Asn Ile Met Pro Gly
                165                 170                 175

Gly Ala Lys Ser Glu Val Phe Met Gln Asn Gln Lys Phe Phe Asp Gly
```

```
                  180                 185                 190
Val Val Lys Thr Ser Thr Asn Leu Asn Ser Asp Pro Val Asp Met Leu
            195                 200                 205

Leu Asn Cys Leu Lys Leu Gly Ile Ser Thr Gly Ile Tyr Gly Leu Thr
        210                 215                 220

Leu Thr Asn Leu Leu Asn Asp Ile Ile Leu Gly Glu Pro Ala Ile Arg
225                 230                 235                 240

Pro Ala Lys Val Gly Phe Lys Val Val Asp Thr Asp Tyr Ile Asn Leu
                245                 250                 255

Met Ile Thr Gly His Gln His Ser Met Ile Ala His Leu Gln Glu Glu
            260                 265                 270

Leu Val Lys Pro Glu Ala Val Lys Ala Gln Ala Val Gly Ala Lys
        275                 280                 285

Gly Phe Lys Leu Val Gly Cys Thr Cys Val Gly Gln Asp Leu Gln Leu
        290                 295                 300

Arg Gly Lys Tyr Tyr Thr Asp Val Phe Ser Gly His Ala Gly Asn Asn
305                 310                 315                 320

Phe Thr Ser Glu Ala Leu Ile Ala Thr Gly Ile Asp Ala Ile Val
                325                 330                 335

Ser Glu Phe Asn Cys Thr Leu Pro Gly Ile Glu Pro Ile Ala Asp Lys
            340                 345                 350

Phe Met Val Lys Met Ile Cys Leu Asp Asp Val Ser Lys Lys Ser Asn
        355                 360                 365

Ala Glu Tyr Val Glu Tyr Ser Phe Lys Asp Arg Glu Lys Ile Ser Asn
        370                 375                 380

His Val Ile Asp Thr Ala Ile Glu Ser Tyr Lys Glu Arg Arg Ser Lys
385                 390                 395                 400

Val Thr Met Asn Ile Pro Lys Asn His Gly Phe Asp Asp Val Ile Thr
                405                 410                 415

Gly Val Ser Glu Gly Ser Leu Lys Ser Phe Leu Gly Gly Ser Trp Lys
            420                 425                 430

Pro Leu Val Asp Leu Ile Ala Ala Gly Lys Ile Lys Gly Val Ala Gly
        435                 440                 445

Ile Val Gly Cys Ser Asn Leu Thr Ala Lys Gly His Asp Val Phe Thr
        450                 455                 460

Val Glu Leu Thr Lys Glu Leu Ile Lys Arg Asn Ile Ile Val Leu Ser
465                 470                 475                 480

Ala Gly Cys Ser Ser Gly Gly Leu Glu Asn Val Gly Leu Met Ser Pro
                485                 490                 495

Gly Ala Ala Glu Leu Ala Gly Asp Ser Leu Lys Glu Val Cys Lys Ser
            500                 505                 510

Leu Gly Ile Pro Pro Val Leu Asn Phe Gly Pro Cys Leu Ala Ile Gly
        515                 520                 525

Arg Leu Glu Ile Val Ala Lys Glu Leu Ala Glu Tyr Leu Lys Ile Asp
        530                 535                 540

Ile Pro Gln Leu Pro Leu Val Leu Ser Ala Pro Gln Trp Leu Glu Glu
545                 550                 555                 560

Gln Ala Leu Ala Asp Gly Ser Phe Gly Leu Ala Leu Gly Leu Pro Leu
                565                 570                 575

His Leu Ala Ile Ser Pro Phe Ile Gly Gly Ser Lys Val Val Thr Lys
            580                 585                 590

Val Leu Cys Glu Asp Met Glu Asn Leu Thr Gly Gly Lys Leu Ile Ile
        595                 600                 605
```

Glu Asp Asp Val Ile Lys Ala Ala Asp Lys Leu Glu Glu Thr Ile Leu
    610                 615                 620

Ala Arg Arg Lys Ser Leu Gly Leu Asn
625                 630

<210> SEQ ID NO 6
<211> LENGTH: 1882
<212> TYPE: DNA
<213> ORGANISM: Clostridium ragsdalei

<400> SEQUENCE: 6

| | | | | | |
|---|---|---|---|---|---|
| atgtcaaata | acaaaatttg | taagtcagca | gataaggtac | ttgaaaagtt | tataggttct | 60 |
| ctagatggtg | tagaaacttc | tcatcatagg | gtagaaagcc | aaagtgttaa | atgtggtttt | 120 |
| ggtcagctag | gagtctgctg | tagactctgt | gcaaacggtc | cctgcagaat | aacacctaaa | 180 |
| gctccaagag | gagtatgtgg | tgctagtgct | gataccatgg | ttgcaagaaa | ctttcttaga | 240 |
| gctgtagctg | ccggcagtgg | atgttatatc | catatagtcg | aaaatacagc | tagaaacgta | 300 |
| aaatcagtag | gtgaaaccgg | cggagagata | aaaggaatga | atgctctcaa | caccctagca | 360 |
| gaaaaacttg | gtataacaga | atctgaccca | cataaaaaag | ctgtactagt | agctgatgcc | 420 |
| gtattaaagg | acttatacaa | accaaaattc | gaaaaaatgg | aagttataaa | taaattagct | 480 |
| tatgcaccta | gactagaaaa | ttggaacaaa | ttaaatataa | tgcctggcgg | tgcaaaatca | 540 |
| gaagtttttt | gatggtgtag | taaaaacttc | tacaaatcta | aacagcgacc | ctgtagatat | 600 |
| gcttctaaat | tgtttaaaac | ttggaatatc | cactgggatt | tacggactta | cccttacaaa | 660 |
| tttattaaat | gacataattt | taggtgaacc | tgctataaga | cctgcaaaag | ttggttttaa | 720 |
| agttgtagat | acggattata | taaatttgat | gataacaggc | caccagcact | ccatgattgc | 780 |
| ccaccttcaa | gaagaacttg | taaaacctga | agctgtaaaa | aaagcccaag | cagttggtgc | 840 |
| taaaggattc | aaactagttg | gatgtacctg | tgtcggacag | gatttacagt | taagaggtaa | 900 |
| atactatact | gatgttttct | ccggtcatgc | aggaaataac | tttacaagtg | aagccttaat | 960 |
| agcaactgga | ggtatagatg | caatagtatc | tgaatttaac | tgtactcttc | ctggcatcga | 1020 |
| gccaatagct | gataagttca | tggttaaaat | gatatgccta | gatgacgttt | ctaaaaaatc | 1080 |
| aaatgcagaa | tatgtagaat | actcttttaa | agatagagaa | aaaataagca | accatgttat | 1140 |
| agatacggct | attgaaagtt | ataaggaaag | aagatctaaa | gttacaatga | atattcctaa | 1200 |
| aaaccatggc | tttgatgacg | tcataacagg | tgtaagtgaa | ggttccttaa | atccttctt | 1260 |
| aggcggaagt | tggaaacctc | ttgtagactt | aattgctgct | ggaaaaatta | aggtgttgc | 1320 |
| tggaatagta | ggttgttcaa | acttaactgc | caaaggtcac | gatgtattta | cagtagaact | 1380 |
| tacaaaagaa | ctcataaaga | gaaatataat | tgtactttct | gcaggttgtt | caagtggtgg | 1440 |
| acttgaaaat | gtaggactta | tgtctccagg | agctgctgaa | cttgcaggag | atagcttaaa | 1500 |
| agaagtatgt | aagagcctag | gtataccacc | tgtactaaat | tttggtccat | gtcttgctat | 1560 |
| tggaagattg | gaaattgtag | caaaagaact | agcagaatac | ctaaaaatag | atattccaca | 1620 |
| gcttccactt | gtgctttctg | cacctcaatg | gcttgaagaa | caagcattgg | cagatggaag | 1680 |
| ttttggtctt | gcccttggat | taccacttca | ccttgctata | tctcctttca | ttggtggaag | 1740 |
| caaagtggta | acaaaagttt | tatgtgaaga | tatggaaaat | ctaacaggcg | gcaagcttat | 1800 |
| aatagaagac | gatgtaataa | aagctgcaga | taaattagaa | gaaaccatac | ttgcaagaag | 1860 |
| gaaaagctta | ggtcttaatt | aa | | | | 1882 |

```
<210> SEQ ID NO 7
<211> LENGTH: 643
<212> TYPE: PRT
<213> ORGANISM: Clostridium ragsdalei

<400> SEQUENCE: 7

Met Ser Gln Thr Thr Leu Glu Lys Asn Glu Thr Ile Arg Glu Arg Thr
  1               5                  10                  15

Glu Gly Arg Val Ser Tyr His Asp Ser Val Glu Glu Met Leu Lys Arg
             20                  25                  30

Ile Arg Glu Asp Gly Met Ser Asn Val Phe Asp Arg Trp Ser Ser Gln
         35                  40                  45

Glu Lys Ile Arg Cys Lys Phe Cys Leu Glu Gly Leu Ser Cys Gln Leu
     50                  55                  60

Cys Ser Gln Gly Pro Cys Arg Ile Asn Leu Lys Gly Glu Gln Lys Lys
 65                  70                  75                  80

Gly Val Cys Gly Ile Gly Pro Asp Ala Met Ala Met Arg Asn Met Leu
                 85                  90                  95

Leu Lys Asn Ile Met Gly Ala Gly Thr Tyr Ser His His Ala Tyr Glu
            100                 105                 110

Ala Phe Arg Thr Leu Arg Glu Thr Gly Glu Gly Lys Thr Pro Phe Thr
        115                 120                 125

Ile Lys Asp Val Asp Lys Leu Lys Trp Met Cys Gln Lys Val Gly Ile
    130                 135                 140

Asn Thr Ser Gly Asp Thr Asn Lys Met Ala Val Asn Leu Ala Asn Phe
145                 150                 155                 160

Leu Glu Ala Glu Met Gly Lys Asp Val Glu Glu Pro Ser Val Met Val
                165                 170                 175

Asp Val Phe Ser Pro Arg Lys Arg Lys Val Trp Lys Asp Leu Gly
                180                 185                 190

Ile Tyr Pro Ser Gly Val Val His Glu Glu Gln Asn Ala Val Ala Ser
            195                 200                 205

Cys Leu Thr Asn Val Asp Gly Asp Tyr Val Ser Leu Ala Lys Lys Ala
        210                 215                 220

Leu Arg Leu Gly Leu Ser Thr Ile Tyr Thr Ala Gln Ile Gly Leu Glu
225                 230                 235                 240

Met Ala Gln Asp Ile Leu Phe Gly Thr Pro Thr Pro His Glu Val Asn
                245                 250                 255

Val Asp Leu Gly Ile Met Asp Pro Glu Tyr Ile Asn Ile Val Phe Asn
            260                 265                 270

Gly His Gln Pro Trp Ala Gly Val Ala Thr Ile Gln Lys Ala Lys Met
        275                 280                 285

Gln Gln Ile Gln Glu Arg Ala Lys Ala Ala Gly Ala Lys Gly Leu Arg
    290                 295                 300

Ile Val Gly Ser Ile Glu Thr Gly Gln Glu Leu Leu Gln Arg Phe Glu
305                 310                 315                 320

Val Asp Asp Val Phe Val Gly Leu Met Gly Asp Trp Leu Ser Ile Glu
                325                 330                 335

Pro Leu Leu Ala Thr Gly Thr Val Asp Val Leu Ala Met Glu Glu Asn
            340                 345                 350

Cys Ser Pro Pro Ala Ile Asp His Tyr Ala Glu Lys Tyr Gln Val Thr
        355                 360                 365

Leu Val Gly Val Ser Thr Ile Ile Gly Ile Pro Gly Leu Asn His Met
    370                 375                 380
```

Ile Pro Tyr Asn Pro Glu Lys Val Gly Glu Met Ala Asp Lys Leu Ile
385                 390                 395                 400

Asp Leu Ala Ile Glu Asn Phe Lys Lys Arg Lys Asp Asn Ile Thr Pro
            405                 410                 415

Lys Val Pro Lys Ile Thr Gln Lys Ala Ile Ala Gly Phe Ser Thr Glu
        420                 425                 430

Ala Val Leu Lys Ala Leu Gly Asn Lys Leu Asp Pro Leu Val Asp Val
            435                 440                 445

Ile Lys Ala Gly Lys Ile Lys Gly Ile Val Ala Leu Ala Asn Cys Ser
450                 455                 460

Thr Leu Arg Asn Gly Pro Gln Asp Trp Asn Thr Val Asn Leu Val Lys
465                 470                 475                 480

Glu Leu Ile Lys Lys Asp Ile Leu Val Val Ala Gly Gly Cys Gly Asn
            485                 490                 495

His Ala Leu Glu Val Ala Gly Leu Cys Asn Leu Asp Ala Ile Asn Met
            500                 505                 510

Ala Gly Gln Gly Leu Lys Glu Val Cys Asn Met Leu Lys Ile Pro Pro
        515                 520                 525

Val Leu Ser Phe Gly Thr Cys Thr Asp Thr Gly Arg Ile Ser Met Leu
530                 535                 540

Val Thr Glu Leu Ala Asn Tyr Leu Asp Val Asp Ile Pro Asp Leu Pro
545                 550                 555                 560

Ile Ala Val Thr Ala Pro Glu Trp Met Glu Gln Lys Ala Thr Ile Asp
            565                 570                 575

Gly Leu Phe Ala Val Ala Tyr Gly Thr Tyr Thr His Leu Ser Pro Thr
        580                 585                 590

Pro Phe Leu Thr Gly Ala Glu Gln Leu Val Lys Leu Leu Thr Glu Asp
    595                 600                 605

Val Glu Ser Leu Thr Gly Gly Lys Val Ala Leu Gly Asp Asn Pro Lys
    610                 615                 620

Glu Ala Ala Asp Asn Ile Glu Ala His Ile Leu Ser Lys Arg Lys Gly
625                 630                 635                 640

Leu Glu Leu

<210> SEQ ID NO 8
<211> LENGTH: 1932
<212> TYPE: DNA
<213> ORGANISM: Clostridium ragsdalei

<400> SEQUENCE: 8
atgagtcaaa ctacactaga aaaaaatgaa actatacgag aaagaacaga agggagagtt      60
agttatcacg attctgtgga gaaatgctt aaaagaatca gggaagatgg tatgtcaaac     120
gtatttgaca gatggtcctc tcaagaaaaa attagatgta agttttgcct agaaggatta     180
agctgtcaat tgtgttctca aggtccctgc agaattaatc ttaaaggaga acagaaaaaa     240
ggtgtttgtg gtattggccc agatgccatg gcaatgcgaa atatgttact taaaaacata     300
atgggagctg gtacatatag ccatcacgca tatgaagcct ttagaacatt aagagaaact     360
ggagaaggca agactccatt tacaattaaa gatgtgata aactcaaatg gatgtgccag     420
aaagtcggaa ttaatacaag cggagatacc aataaaatgg cagtgaatct ggcaaatttt     480
ttggaagctg agatgggtaa agatgtgaa gaacctagtg ttatggtaga tgtgttttca     540
ccaagaaaga gaaaaaaagt ttggaaagat cttggaattt atccttcagg agtagttcac     600

```
gaagagcaaa atgcagtagc aagttgttta acaaatgttg atggggatta tgtatcatta        660
gctaaaaaag cgctgcggct aggtctgtca actatctata cagcacaaat aggacttgaa        720
atggctcagg atatactttt tggcacgcct acaccccatg aggtaaatgt ggacttagga        780
attatggatc cagagtatat aaatattgta tttaatggac atcaaccttg gctggtgtt         840 gctactattc aaaaggcaaa gatgcagcag atacaggaaa gagcaaaggc agctggtgca        900
aaagggctta aatagttgg gtcaattgaa acaggacagg aattattaca agatttgag         960 gtagatgatg tatttgtagg tttaatggga gattggctat ctatagaacc acttcttgct       1020
acaggtacag ttgatgttct tgcaatgaaa gaaaactgtt ctccacctgc aatagatcat       1080
tatgctgaaa gtatcaggt aactttagta ggtgtaagta ctattatagg tattccgggg        1140
ttaaatcata tgattccata taatcctgaa aaagtgggtg aaatggctga taaattgatt       1200
gatttggcca ttgaaaattt taaaaagaga aaggataaca ttacaccaaa ggttcctaaa       1260
ataacacaga aagcaatagc agggttttct actgaagcag ttttaaaagc tttaggaaat       1320
aagcttgatc cacttgttga tgttattaag gcagggaaga ttaaaggaat tgtggctttg       1380
gcaaattgtt caactctaag aaatggtcct caagattgga atacagttaa cctggtaaag      1440
gaattgatta aaaaggatat tttagttgtg gctggtgggt gcggcaatca tgctcttgaa      1500
gtagcagggc tgtgcaacct agatgcaata acatggctg ccaaggact aaaagaagta        1560 tgcaatatgc taaagattcc tccagttcta agctttggaa cttgtacaga tacgggaaga      1620
atatccatgc ttgttacaga acttgctaat taccttgatg tagatatacc agatcttcct      1680
attgctgtaa cggctcctga gtggatgaa caaaaagcta ctatagatgg tttatttgca       1740
gtagcctatg ggacatatac acattatct ccaactccat ttctaacagg cgcagaacag       1800
cttgtaaagc ttcttactga ggatgtagag agcttaacag gaggtaaagt tgcattagga      1860
gataatccaa agaggcagc tgataatatt gaagcacata tattaagtaa agaaagggt        1920 ttggagttat aa                                                            1932
```

<210> SEQ ID NO 9
<211> LENGTH: 639
<212> TYPE: PRT
<213> ORGANISM: Clostridium scatologenes

<400> SEQUENCE: 9

```
Met Ser Glu Thr Ile Leu Glu Lys Ser Glu Gly Arg Val Ser Tyr His
1               5                   10                  15

Asp Ser Val Glu Glu Met Ile Lys Arg Ile Arg Glu Asp Gly Met Ser
                20                  25                  30

Asn Ala Phe Asp Arg Tyr Ala Leu Gln Asp Lys Ile Arg Cys Lys Phe
            35                  40                  45

Cys Leu Glu Gly Leu Ser Cys Gln Leu Cys Ser Asn Gly Pro Cys Arg
        50                  55                  60

Ile Ser Glu Lys Thr Gly Gln Thr Lys Gly Val Cys Gly Ile Ser Ala
65                  70                  75                  80

Asp Ala Met Ala Met Arg Asn Phe Leu Leu Lys Asn Ile Met Gly Ala
                85                  90                  95

Gly Thr Tyr Ser His His Ala Tyr Glu Ala Phe Arg Thr Leu Lys Ala
            100                 105                 110

Thr Ala Glu Gly Lys Thr Pro Phe Lys Ile Thr Asp Val Asn Lys Leu
        115                 120                 125

Lys Trp Met Cys Glu Lys Val Gly Ile Asn Thr Asn Gln Glu Ile Asn
```

-continued

```
            130                 135                 140

Asp Met Ala Ile Glu Leu Ala Val Leu Leu Glu Asp Gln Gln Ile Ile
145                 150                 155                 160

Gly Ile Glu Asp Lys Asn Ile Met Ile Glu Ala Phe Ala Pro Lys Lys
                165                 170                 175

Arg Lys Glu Leu Trp Arg Lys Leu Asp Ile Tyr Pro Gly Gly Thr Val
            180                 185                 190

His Glu Glu Gln Asn Cys Val Ala Ser Cys Leu Thr Asn Val Asp Gly
        195                 200                 205

Ser His Val Ser Leu Ala Met Lys Ala Leu Arg Leu Gly Ile Ala Thr
    210                 215                 220

Ile Tyr Asn Ser Gln Ile Gly Leu Glu Met Val Gln Asp Ile Leu Phe
225                 230                 235                 240

Gly Thr Pro Thr Pro His Glu Val Asn Met Asp Leu Gly Ile Met Asp
                245                 250                 255

Pro Glu Tyr Val Asn Ile Val Phe Asn Gly His Gln Pro Trp Pro Gly
            260                 265                 270

Val Ala Thr Ile Leu Lys Ala Arg Thr Lys Glu Val Gln Glu Lys Ala
        275                 280                 285

Lys Ala Ala Gly Ala Lys Gly Leu Arg Ile Val Gly Ser Ile Glu Thr
    290                 295                 300

Gly Gln Glu Leu Leu Gln Arg Phe Glu Ile Asp Asp Val Phe Val Gly
305                 310                 315                 320

His Met Gly Asn Trp Leu Thr Ile Glu Pro Leu Leu Ala Thr Gly Thr
                325                 330                 335

Val Asp Val Phe Ala Met Glu Glu Asn Cys Ser Pro Pro Ala Ile Asp
            340                 345                 350

Met Tyr Ala Glu Lys Tyr Gln Val Thr Leu Val Ser Val Ser Thr Ile
        355                 360                 365

Ile Asp Leu Pro Gly Leu Asp Glu Lys Ile Pro Tyr Asp Pro Ser Lys
    370                 375                 380

Val Asn Ala Met Ala Asp Arg Leu Ile Glu Leu Ala Ile Gln Asn Phe
385                 390                 395                 400

Lys Lys Arg Lys Glu Arg Asn Ile Gln Pro Met Val Pro Lys Lys Ile
                405                 410                 415

Gln Lys Ala Ile Ala Gly Phe Ser Thr Glu Ala Val Leu Gly Ala Leu
            420                 425                 430

Gly Asn Lys Leu Asp Pro Leu Val Asp Val Ile Ala Ala Gly Lys Ile
        435                 440                 445

Lys Gly Val Val Ala Leu Ala Asn Cys Ser Thr Leu Arg Asn Gly Pro
    450                 455                 460

Gln Asp Trp Val Thr Ile Asn Leu Thr Lys Glu Leu Ile Lys Lys Asp
465                 470                 475                 480

Ile Leu Val Val Ser Gly Gly Cys Gly Asn His Ala Leu Glu Val Ala
                485                 490                 495

Gly Leu Cys Thr Val Glu Ala Ala Asn Glu Leu Ala Gly Glu Gly Leu
            500                 505                 510

Lys Glu Val Cys Asn Met Leu Lys Ile Pro Pro Val Leu Ser Phe Gly
        515                 520                 525

Thr Cys Thr Asp Thr Gly Arg Ile Ser Met Leu Val Thr Ala Leu Ala
    530                 535                 540

Asp His Leu Asp Val Asp Val Ser Asp Leu Pro Ile Ala Val Thr Ala
545                 550                 555                 560
```

```
Pro Glu Trp Met Glu Gln Lys Ala Thr Ile Asp Gly Ile Phe Ala Leu
            565                 570                 575
Ala Tyr Gly Ala Tyr Thr His Leu Ser Pro Thr Pro Phe Met Thr Gly
        580                 585                 590
Ala Pro Gln Leu Val Glu Leu Leu Thr Lys Lys Val Glu Asp Val Thr
    595                 600                 605
Gly Gly Lys Ile Ala Leu Gly Asp Asn Pro Val Glu Val Ala Asn Asn
610                 615                 620
Ile Glu Ala His Ile Ile Ser Lys Arg Lys Gly Leu Gly Leu Ser
625                 630                 635

<210> SEQ ID NO 10
<211> LENGTH: 1920
<212> TYPE: DNA
<213> ORGANISM: Clostridium scatologenes

<400> SEQUENCE: 10
```

| | |
|---|---|
| atgagtgaaa ctatactaga aaatcagaa ggtagagtaa gttatcatga ttctgtagaa | 60 |
| gaaatgatca aagaattag agaagatgga atgtctaatg catttgatag atatgcactt | 120 |
| caagacaaaa ttaggtgcaa attttgcctt gagggtttaa gttgtcaatt atgttcaaat | 180 |
| ggtccatgta gaataagtga gaaaacaggt caaactaaag gtgtatgtgg aatatctgct | 240 |
| gatgcaatgg caatgagaaa ttttctttta aaaaatataa tgggcgcagg tacatatagt | 300 |
| catcatgctt atgaagcttt tagaacattg aaagctacag cagaaggaaa aactccattt | 360 |
| aaaattacag atgtaaataa acttaaatgg atgtgtgaaa agtaggtat aaatacaaat | 420 |
| caagaaatca atgatatggc catagaatta gctgttctac ttgaagatca acaaataatt | 480 |
| ggtatagaag ataagaacat catgattgaa gcttttgcac aaaaaaaag aaaagaatta | 540 |
| tggaggaaac tagatatata tcctggtgga acagttcacg aagaacaaaa ttgtgtagct | 600 |
| agttgtctta caaatgtaga tggaagccat gtttctttag ctatgaaagc tcttagactc | 660 |
| ggtatagcaa ctatatataa ttctcaaata ggtctagaaa tggttcaaga catattattt | 720 |
| ggaacaccaa ccccacatga agttaatatg gatttaggaa ttatggaccc agaatatgta | 780 |
| aacatagtat ttaatggtca tcaaccttgg cctggagttg ccactatatt aaaagcaaga | 840 |
| actaaagaag ttcaagaaaa agcaaaagct gctggtgcta aaggacttag aatagttggt | 900 |
| tcaatagaaa cagggcaaga attattgcaa agatttgaaa tagatgatgt atttgtgggt | 960 |
| catatgggaa actggcttac tatagaacca ttgttagcta ctggtactgt agatgtcttt | 1020 |
| gcaatggaag aaaattgctc gccaccagct attgatatgt atgctgaaaa atatcaagta | 1080 |
| actttagtat ctgtaagtac tataattgat ctaccaggtc ttgatgaaaa aattccttat | 1140 |
| gatccttcta agtgaacgc tatggctgat agattaattg aacttgctat acaaaatttt | 1200 |
| aaaaagagaa aagaaagaaa tattcaacca atggttccta aaaaaattca aaaagctata | 1260 |
| gctgggttct caactgaagc tgtgttaggc gctcttggaa ataaacttga tcctttagta | 1320 |
| gatgtaatag ctgctgggaa attaagggga gttgtagctc ttgcaaattg ttctactta | 1380 |
| agaaatggtc ctcaagactg ggttacaata atcttacaa aagagcttat aaaaaaagat | 1440 |
| atattagttg ttagtggtgg ctgtggaaat catgctcttg aagttgcagg attatgtaca | 1500 |
| gtagaagcag ctaatgaatt agctggtgaa ggattaaaag aagtatgcaa tatgttaaaa | 1560 |
| atccctccag tactaagctt tggaacctgt actgatacag gtagaatatc tatgcttgtt | 1620 |
| actgctctag cagatcattt ggatgttgat gtatctgacc ttccaatagc tgttactgct | 1680 |

-continued

```
ccagaatgga tggagcaaaa agcaaccata gatggaattt ttgcattagc ctatggagct    1740
tatactcatt tatctcctac tccttttatg acaggagctc ctcagcttgt agagcttcta    1800
actaaaaaag tagaagatgt aacaggtgga aaaatcgcac taggagataa tcctgttgag    1860
gttgcaaaca atatagaggc tcacataata agtaaaagaa aagggttagg attaagttaa    1920
```

<210> SEQ ID NO 11
<211> LENGTH: 400
<212> TYPE: PRT
<213> ORGANISM: Clostridium scatologenes

<400> SEQUENCE: 11

```
Met Glu Glu Lys Ala Lys Ser Ile Asp Gln Ala Thr Leu Gln Leu Leu
1               5                   10                  15

Asp Lys Ala Lys Gln Asp Gly Val Glu Thr Val Trp Asp Arg Lys Ala
            20                  25                  30

Asp Met Lys Val Gln Cys Gly Phe Gly Ser Ala Gly Val Cys Cys Arg
        35                  40                  45

Asn Cys Ser Met Gly Pro Cys Arg Val Ser Pro Val Pro Gly Lys Gly
    50                  55                  60

Val Glu Arg Gly Ile Cys Gly Ala Thr Ala Asp Val Ile Val Ser Arg
65                  70                  75                  80

Asn Phe Ala Arg Met Val Ala Gly Thr Ala His Ser Asp His
                85                  90                  95

Gly Arg Ser Ile Ala Leu Ser Leu Tyr His Thr Ser Lys Asp Gly Asp
            100                 105                 110

Ile Lys Val Lys Asp Glu Asn Lys Leu Lys Glu Val Ala Lys Ser Phe
        115                 120                 125

Asn Val Glu Thr Glu Gly Arg Asp Ile Tyr Asp Ile Ala His Asp Val
    130                 135                 140

Ala Lys Glu Gly Leu Ser Asn Tyr Gly Lys Gln Leu Gly Glu Val Thr
145                 150                 155                 160

Leu Pro Pro Ser Leu Pro Glu Lys Arg Lys Glu Leu Trp Arg Lys Leu
                165                 170                 175

Gly Val Tyr Pro Arg Ala Val Asp Arg Glu Ile Ala Ala Val Met His
            180                 185                 190

Ser Thr His Ile Gly Cys Asn Ala Asp Ala Glu Ala Met Ile Lys Met
        195                 200                 205

Ser Met Arg Cys Ser Leu Thr Asp Gly Trp Met Gly Ser Phe Met Gly
    210                 215                 220

Thr Glu Phe Ser Asp Ile Met Phe Gly Thr Pro His Ser Ile Asp Thr
225                 230                 235                 240

Glu Ala Asn Leu Gly Val Leu Glu Lys Asn Ser Val Asn Val Val Leu
                245                 250                 255

His Gly His Glu Pro Leu Leu Ser Glu Met Val Val Glu Ala Ala Ser
            260                 265                 270

Asp Pro Glu Leu Val Glu Leu Ala Lys Ser Val Gly Ala Asp Gly Ile
        275                 280                 285

Asn Leu Cys Gly Met Cys Cys Thr Gly Asn Glu Val Ser Met Arg His
    290                 295                 300

Gly Ile Lys Ile Ala Gly Asn Phe Met Gln Gln Glu Leu Ala Val Val
305                 310                 315                 320

Thr Gly Ala Val Asp Gly Leu Ile Val Asp Val Gln Cys Ile Met Pro
                325                 330                 335
```

Ala Leu Ala Lys Leu Ser Lys Ser Tyr His Thr Lys Phe Ile Thr Thr
            340                 345                 350

Ser Pro Lys Ala His Ile Thr Asp Ser Ile Tyr Met Glu Phe Asp Glu
        355                 360                 365

Glu Asn Pro Leu Asp Ser Ala Lys Lys Ile Leu Lys Glu Ala Ile Leu
370                 375                 380

Asn Phe Lys Asn Arg Asp Gln Ser Lys Val Met Ile Pro Glu Leu Lys
385                 390                 395                 400

<210> SEQ ID NO 12
<211> LENGTH: 1278
<212> TYPE: DNA
<213> ORGANISM: Clostridium scatologenes

<400> SEQUENCE: 12

| | | | | | |
|---|---|---|---|---|---|
| atggaagaaa | aagcaaaatc | aattgatcag | gctactttac | aattattgga | caaggcaaaa | 60 |
| caagatgggg | tcgaaacagt | ttgggataga | aaagcagaca | tgaaggtaca | gtgtggattt | 120 |
| ggatcagcag | gagtttgctg | tagaaattgc | agcatgggcc | catgtagagt | aagtccagtg | 180 |
| ccaggaaaag | gtgtagaaag | aggtatatgt | ggagctacag | cagatgtaat | tgtatctaga | 240 |
| aattttgcaa | gaatggttgc | agcaggtact | gcagcacact | cagatcatgg | tagaagtata | 300 |
| gcacttagct | tgtatcacac | tagtaaagat | ggagatataa | agttaaaga | tgaaaataaa | 360 |
| ttgaaagaag | ttgcaaagag | ctttaatgtt | gaaactgagg | aagagatat | atatgacata | 420 |
| gctcatgatg | tagcaaaaga | aggattaagt | aattatggta | acagcttgg | agaagttact | 480 |
| ttaccacctt | ctttaccaga | aaagagaaaa | gaattgtgga | gaaaattagg | tgtatatcca | 540 |
| agggcagttg | atagagaaat | agctgcagtt | atgcattcaa | cacatatagg | atgtaatgca | 600 |
| gatgcagaag | ctatgattaa | aatgtctatg | agatgttcac | taactgatgg | atggatgggc | 660 |
| tcattcatgg | gaacagaatt | cagtgatata | atgtttggaa | cacctcattc | cattgataca | 720 |
| gaggcaaatc | ttggagtact | tgaaaagaat | tctgtaaatg | tagttttaca | cggacatgaa | 780 |
| ccacttcttt | cagaaatggt | agtagaagca | gcatcagatc | cagagttagt | tgaacttgct | 840 |
| aaatcagtag | gtgctgatgg | aataaattta | tgtggaatgt | gctgtactgg | aaatgaagtt | 900 |
| tccatgagac | atggcatcaa | aatagcagga | aactttatgc | agcaggaatt | ggctgtagtt | 960 |
| acaggagcag | tagatggact | tatagttgat | gtacagtgta | ttatgccagc | actagcaaaa | 1020 |
| ttgtccaagt | catatcatac | taagtttata | acaacttcac | caaaggcaca | catcacagat | 1080 |
| tcaatttata | tggaatttga | tgaagaaaac | ccacttgatt | cagctaagaa | gattctaaaa | 1140 |
| gaagcaatat | taaactttaa | aaatagagat | cagagcaaag | taatgattcc | tgaattgaaa | 1200 |
| tgaaaggcaa | ttttgggata | cagtgttgaa | gaattataa | ataaattaga | caaggttgta | 1260 |
| aatacacaaa | taggacca | | | | | 1278 |

<210> SEQ ID NO 13
<211> LENGTH: 227
<212> TYPE: PRT
<213> ORGANISM: Clostridium scatologenes

<400> SEQUENCE: 13

Met Gly Tyr Ser Val Glu Glu Ile Ile Asn Lys Leu Asp Lys Val Val
1               5                   10                  15

Asn Thr Gln Ile Gly Pro Met Gln Thr Val Lys Pro Leu Ala Asp Val
            20                  25                  30

| | | | | | | | | | | |
|---|---|---|---|---|---|---|---|---|---|---|
| Leu | Val | Ser | Gly | Val | Leu | Arg | Gly | Ala | Ala | Ala | Val | Gly | Cys | Asn |
| | | 35 | | | | 40 | | | | 45 | | | | |
| Asn | Pro | Lys | Val | Val | Gln | Asp | Ser | Ala | His | Ile | Glu | Thr | Ile | Lys | Gly |
| 50 | | | | | 55 | | | | | 60 | | | | | |
| Leu | Ile | Lys | Asn | Asp | Val | Ile | Val | Val | Thr | Gly | Cys | Ala | Ala | Gln |
| 65 | | | | 70 | | | | | 75 | | | | | 80 |
| Ala | Ala | Ala | Lys | Tyr | Gly | Leu | Leu | Gln | Lys | Glu | Ala | Ala | Glu | Lys | Tyr |
| | | | | 85 | | | | | 90 | | | | | 95 | |
| Ala | Gly | Pro | Gly | Leu | Ala | Thr | Val | Cys | Lys | Leu | Val | Asp | Ile | Pro | Pro |
| | | | 100 | | | | | 105 | | | | | 110 | | |
| Val | Leu | His | Met | Gly | Ser | Cys | Val | Asp | Ile | Ser | Arg | Ile | Leu | Asp | Leu |
| | | 115 | | | | | 120 | | | | | 125 | | | |
| Val | Gly | Arg | Val | Ala | Asn | Leu | Leu | Gly | Val | Asp | Met | Ser | Asp | Leu | Pro |
| | 130 | | | | | 135 | | | | | 140 | | | | |
| Val | Ala | Gly | Val | Ala | Pro | Glu | Trp | Met | Ser | Glu | Lys | Ala | Val | Ala | Ile |
| 145 | | | | | 150 | | | | | 155 | | | | | 160 |
| Gly | Thr | Tyr | Val | Val | Thr | Ser | Gly | Ile | Asp | Thr | Trp | Leu | Gly | Val | Ala |
| | | | | 165 | | | | | 170 | | | | | 175 | |
| Pro | Pro | Val | Thr | Gly | Gly | Pro | Glu | Val | Val | Asp | Ile | Leu | Thr | Asn | Lys |
| | | | 180 | | | | | 185 | | | | | 190 | | |
| Met | Glu | Asp | Trp | Val | Gly | Ala | Lys | Phe | Phe | Ile | Glu | Thr | Asp | Pro | His |
| | | | 195 | | | | | 200 | | | | | 205 | | |
| Lys | Ala | Val | Glu | Gln | Ile | Val | Asn | Arg | Met | Asn | Glu | Lys | Arg | Lys | Lys |
| | 210 | | | | | 215 | | | | | 220 | | | | |
| Leu | Gly | Ile |
| 225 | | |

<210> SEQ ID NO 14
<211> LENGTH: 617
<212> TYPE: DNA
<213> ORGANISM: Clostridium scatologenes

<400> SEQUENCE: 14

```
atgcaaactg taaaacctt tggcagatgtt ttagtatcag gagtattaag aggtgctgca      60
gctgtggttg gatgtaataa tcctaaagtt gtacaagatt ctgcacacat tgaaactata     120
aaaggattaa taaaaaatga tgtaattgtt gttgttacag gttgtgcagc tcaagcagca     180
gcaaaatatg gcttattaca aaaagaagca gcagaaaaat atgcaggacc aggactagct     240
actgtatgta aacttgtaga cataccacct gtacttcata tggggttcttg tgttgatata     300
agtcgtatat tagatttggt tggaagagtg gctaattat tgggcgttga catgagtgac      360
cttccagttg caggtgtagc acctgaatgg atgtcagaaa aagccgtagc aataggtact     420
tatgtagtaa cttcaggtat agatacttgg cttggagtag cacctccagt aacaggcggc     480
ccagaagttg ttgacattct tactaataag atggaagact gggtaggagc taaattcttt     540
atagaaacag atcctcataa agcagttgaa caaattgtaa ataggatgaa tgaaaaacgt     600
aaaaaattag gtatcta                                                    617
```

<210> SEQ ID NO 15
<211> LENGTH: 617
<212> TYPE: DNA
<213> ORGANISM: Artificial sequence
<220> FEATURE:
<223> OTHER INFORMATION: Synthetic

<400> SEQUENCE: 15

```
atgcaaactg taaaacctttt ggcagatgtt ttagtatcag gagtattaag aggtgctgca    60
gctgtggttg gatgtaataa tcctaaagtt gtacaagatt ctgcacacat tgaaactata   120
aaaggattaa taaaaaatga tgtaattgtt gttgttacag gttgtgcagc tcaagcagca   180
gcaaaatatg gcttattaca aaaagaagca gcagaaaaat atgcaggacc aggactagct   240
actgtatgta aacttgtaga cataccacct gtacttcata tgggttcttg tgttgatata   300
agtcgtatat tagatttggt tggaagagtg gctaatttat tgggcgttga catgagtgac   360
cttccagttg caggtgtagc acctgaatgg atgtcagaaa aagccgtagc aataggtact   420
tatgtagtaa cttcaggtat agatacttgg cttggagtag cacctccagt aacaggcggc   480
ccagaagttg ttgacattct tactaataag atggaagact gggtaggagc taaattcttt   540
atagaaacag atcctcataa agcagttgaa caaattgtaa ataggatgaa tgaaaaacgt   600
aaaaaattag gtatcta                                                  617

<210> SEQ ID NO 16
<211> LENGTH: 344
<212> TYPE: DNA
<213> ORGANISM: Artificial sequence
<220> FEATURE:
<223> OTHER INFORMATION: Synthetic

<400> SEQUENCE: 16
aagcttataa ttatccttaa gtgtcatggt agtgcgccca gatagggtgt taagtcaagt    60
agtttaaggt actactctgt aagataacac agaaacagc caacctaacc gaaaagcgaa    120
agctgatacg ggaacagagc acggttggaa agcgatgagt tacctaaaga caatcgggta   180
cgactgagtc gcaatgttaa tcagatataa ggtataagtt gtgtttactg aacgcaagtt   240
tctaatttcg attacacttc gatagaggaa agtgtctgaa acctctagta caaagaaagg   300
taagttatct accatgactt atctgttatc accacatttg taca                    344

<210> SEQ ID NO 17
<211> LENGTH: 344
<212> TYPE: DNA
<213> ORGANISM: Artificial sequence
<220> FEATURE:
<223> OTHER INFORMATION: Synthetic

<400> SEQUENCE: 17
aagcttataa ttatccttag agttcgctgt agtgcgccca gatagggtgt taagtcaagt    60
agtttaaggt actactctgt aagataacac agaaacagc caacctaacc gaaaagcgaa    120
agctgatacg ggaacagagc acggttggaa agcgatgagt tacctaaaga caatcgggta   180
cgactgagtc gcaatgttaa tcagatataa ggtataagtt gtgtttactg aacgcaagtt   240
tctaatttcg attaactctc gatagaggaa agtgtctgaa acctctagta caaagaaagg   300
taagttatct acagcgactt atctgttatc accacatttg taca                    344

<210> SEQ ID NO 18
<211> LENGTH: 562
<212> TYPE: DNA
<213> ORGANISM: Clostridium autoethanogenum

<400> SEQUENCE: 18
ggccgcagat agtcataata gttccagaat agttcaattt agaaattaga ctaaacttca    60
aaatgtttgt taaatatata ccaaactagt atagatattt tttaaatact ggacttaaac   120
agtagtaatt tgcctaaaaa attttttcaa tttttttttaa aaaatccttt tcaagttgta   180
```

```
cattgttatg gtaatatgta attgaagaag ttatgtagta atattgtaaa cgtttcttga      240 ttttttaca tccatgtagt gcttaaaaaa ccaaaatatg tcacatgcaa ttgtatattt      300
caaataacaa tatttatttt ctcgttaaat tcacaaataa tttattaata atatcaataa      360
ccaagattat acttaaatgg atgttttattt tttaacactt ttatagtaaa tatatttatt     420
ttatgtagta aaaaggttat aattataatt gtatttatta caattaatta aaataaaaat     480
agggttttag gtaaaattaa gttattttaa gaagtaatta cataaaaaat tgaagttatt     540
gctttaagga gggaattatt ca                                              562
```

<210> SEQ ID NO 19
<211> LENGTH: 573
<212> TYPE: DNA
<213> ORGANISM: Clostridium autoethanogenum

<400> SEQUENCE: 19

```
atggataatt tagttataaa tacattgaaa gaagtaggag cacttttgga agggcatttt      60
ctactttctt caggaaaaca cagtgatagg tattgtcagt gtgcaaaact tttacagtat      120
cctgacaggg caaagatgt aatagcagtt attgcagaca aattagagaa tgttgactat      180
gataaaatag ttggacctgc aatgggggg atattagttt cctatgaact tgcaaggcaa      240
acgggcaaac caggaatatt tgctgaaagg caaaatggaa atatgactat aagaagggga      300
tttgaaataa agaaggaga aaaaattata atttctgaag atgtggtaac tacaggaaaa      360
tcatctgtag aggttgctaa ggtaattcag gaattaggtg gagaggttgt aggcatatgt      420
tgcatagtag acagaagagc agaaggtgtc aaaatagaat atccaattta tagtgcagta      480
aaacttaata taaacactta tgataaggaa aattgtccta tgtgtaagca aggacaagaa      540
tatgtaaagc ctggaagtag agtattcaaa taa                                  573
```

<210> SEQ ID NO 20
<211> LENGTH: 6927
<212> TYPE: DNA
<213> ORGANISM: Artificial sequence
<220> FEATURE:
<223> OTHER INFORMATION: Synthetic

<400> SEQUENCE: 20

```
cctgcaggat aaaaaaattg tagataaatt ttataaaata gttttatcta caatttttttt    60 atcaggaaac agctatgacc gcggccgcag atagtcataa tagttccaga atagttcaat    120
ttagaaatta gactaaactt caaaatgttt gttaaatata taccaaacta gtatagatat    180
tttttaaata ctggacttaa acagtagtaa tttgcctaaa aaatttttc aattttttttt    240 aaaaaatcct tttcaagttg tacattgtta tggtaatatg taattgaaga agttatgtag    300
taatattgta aacgtttctt gatttttttta catccatgta gtgcttaaaa aaccaaaata   360
tgtcacatgc aattgtatat ttcaaataac aatatttatt ttctcgttaa attcacaaat    420
aatttattaa taatatcaat aaccaagatt atacttaaat ggatgtttat tttttaacac    480
ttttatagta aatatattta ttttatgtag taaaaaggtt ataattataa ttgtatttat    540
tacaattaat taaaataaaa atagggttt aggtaaaatt aagttatttt aagaagtaat    600
tacaataaaa attgaagtta ttgctttaag gagggaatta ttcatatgga agaaaaagca   660
aaatcaattg atcaggctac tttacaatta ttggacaagg caaaacaaga tgggggtcgaa   720 acagtttggg atagaaaagc agacatgaag gtacagtgtg gatttggatc agcaggagtt   780
```

```
tgctgtagaa attgcagcat gggcccatgt agagtaagtc cagtgccagg aaaaggtgta    840
gaaagaggta tatgtggagc tacagcagat gtaattgtat ctagaaattt tgcaagaatg    900
gttgcagcag gtactgcagc acactcagat catggtagaa gtatagcact tagcttgtat    960
cacactagta aagatggaga tataaaagtt aaagatgaaa ataaattgaa agaagttgca   1020
aagagcttta atgttgaaac tgagggaaga gatatatatg acatagctca tgatgtagca   1080
aaagaaggat taagtaatta tggtaaacag cttggagaag ttactttacc accttcttta   1140
ccagaaaaga gaaaagaatt gtggagaaaa ttaggtgtat atccaagggc agttgataga   1200
gaaatagctg cagttatgca ttcaacacat ataggatgta atgcagatgc agaagctatg   1260
attaaaatgt ctatgagatg ttcactaact gatggatgga tgggctcatt catgggaaca   1320
gaattcagtg atataatgtt tggaacacct cattccattg atacagaggc aaatcttgga   1380
gtacttgaaa agaattctgt aaatgtagtt ttacacggac atgaaccact tctttcagaa   1440
atggtagtag aagcagcatc agatccagag ttagttgaac ttgctaaatc agtaggtgct   1500
gatggaataa atttatgtgg aatgtgctgt actggaaatg aagtttccat gagacatggc   1560
atcaaaatag caggaaactt tatgcagcag gaattggctg tagttacagg agcagtagat   1620
ggacttatag ttgatgtaca gtgtattatg ccagcactag caaaattgtc caagtcatat   1680
catactaagt ttataacaac ttcaccaaag gcacacatca cagattcaat ttatatggaa   1740
tttgatgaag aaaacccact tgattcagct aagaagattc taaagaagc aatattaaac   1800 tttaaaaata gagatcagag caaagtaatg attcctgaat tgaaatgaaa ggcaattttg   1860
ggatacagtg ttgaagaaat tataaataaa ttagacaagg ttgtaaatac acaaatagga   1920
ccaatgcaaa ctgtaaaacc tttggcagat gttttagtat caggagtatt aagaggtgct   1980
gcagctgtgg ttgatgtaa taatcctaaa gttgtacaag attctgcaca cattgaaact   2040
ataaaaggat taataaaaaa tgatgtaatt gttgttgtta caggttgtgc agctcaagca   2100
gcagcaaaat atggcttatt acaaaaagaa gcagcagaaa aatatgcagg accaggacta   2160
gctactgtat gtaaacttgt agacatacca cctgtacttc acatgggttc ttgtgttgat   2220
ataagtcgta tattagattt ggttggaaga gtggctaatt tattgggcgt tgacatgagt   2280
gaccttccag ttgcaggtgt agcacctgaa tggatgtcag aaaaagccgt agcaataggt   2340
acttatgtag taacttcagg tatagatact tggcttggag tagcacctcc agtaacaggc   2400
ggcccagaag ttgttgacat tcttactaat aagatggaag actgggtagg agctaaattc   2460
tttatagaaa cagatcctca taaagcagtt gaacaaattg taaataggat gaatgaaaaa   2520
cgtaaaaaat taggtatcta ataataaaga caagcaattg ccatgccaga gctcggtacc   2580
cggggatcct ctagagtcga cgtcacgcgt ccatggagat ctcgaggcct gcagacatgc   2640
aagcttggca ctggccgtcg ttttacaacg tcgtgactgg gaaaaccctg gcgttaccca   2700
acttaatcgc cttgcagcac atccccctt cgccagctgg cgtaatagcg aagaggcccg   2760
caccgatcgc ccttcccaac agttgcgcag cctgaatggc gaatggcgct agcataaaaa   2820
taagaagcct gcatttgcag gcttcttatt tttatggcgc gccgccatta ttttttttgaa   2880 caattgacaa ttcatttctt atttttttatt aagtgatagt caaaaggcat aacagtgctg   2940
aatagaaaga aatttacaga aagaaaatt atagaattta gtatgattaa ttatactcat   3000
ttatgaatgt ttaattgaat acaaaaaaaa atacttgtta tgtattcaat tacgggttaa   3060
aatatagaca agttgaaaaa tttaataaaa aaataagtcc tcagctctta tatattaagc   3120
taccaactta gtatataagc caaaacttaa atgtgctacc aacacatcaa gccgttagag   3180
```

```
aactctatct atagcaatat ttcaaatgta ccgacataca agagaaacat taactatata   3240
tattcaattt atgagattat cttaacagat ataaatgtaa attgcaataa gtaagattta   3300
gaagtttata gcctttgtgt attggaagca gtacgcaaag gcttttttat ttgataaaaa   3360
ttagaagtat atttattttt tcataattaa tttatgaaaa tgaaaggggg tgagcaaagt   3420
gacagaggaa agcagtatct tatcaaataa caaggtatta gcaatatcat tattgacttt   3480
agcagtaaac attatgactt ttatagtgct tgtagctaag tagtacgaaa gggggagctt   3540
taaaaagctc cttggaatac atagaattca taaattaatt tatgaaaaga agggcgtata   3600
tgaaaacttg taaaaattgc aaagagttta ttaaagatac tgaaatatgc aaaatacatt   3660
cgttgatgat tcatgataaa acagtagcaa cctattgcag taaatacaat gagtcaagat   3720
gtttacataa agggaaagtc caatgtatta attgttcaaa gatgaaccga tatggatggt   3780
gtgccataaa aatgagatgt tttacagagg aagaacagaa aaaagaacgt acatgcatta   3840
aatattatgc aaggagcttt aaaaaagctc atgtaaagaa gagtaaaaag aaaaaataat   3900
ttatttatta atttaatatt gagagtgccg acacagtatg cactaaaaaa tatatctgtg   3960
gtgtagtgag ccgatacaaa aggatagtca ctcgcatttt cataatacat cttatgttat   4020
gattatgtgt cggtgggact tcacgacgaa aacccacaat aaaaaaagag ttcggggtag   4080
ggttaagcat agttgaggca actaaacaat caagctagga tatgcagtag cagaccgtaa   4140
ggtcgttgtt taggtgtgtt gtaatacata cgctattaag atgtaaaaat acggatacca   4200
atgaagggaa aagtataatt tttgatgta gtttgtttgt tcatctatgg gcaaactacg   4260
tccaaagccg tttccaaatc tgctaaaaag tatatccttt ctaaaatcaa agtcaagtat   4320
gaaatcataa ataaagttta attttgaagt tattatgata ttatgttttt ctattaaaat   4380
aaattaagta tatagaatag tttaataata gtatatactt aatgtgataa gtgtctgaca   4440
gtgtcacaga aaggatgatt gttatggatt ataagcggcc ggccagtggg caagttgaaa   4500
aattcacaaa aatgtggtat aatatctttg ttcattagag cgataaactt gaatttgaga   4560
gggaacttag atggtatttg aaaaaattga taaaaatagt tggaacagaa aagagtattt   4620
tgaccactac tttgcaagtg taccttgtac ctacagcatg accgttaaag tggatatcac   4680
acaaataaag gaaagggaa tgaaactata tcctgcaatg ctttattata ttgcaatgat   4740
tgtaaaccgc cattcagagt ttaggacggc aatcaatcaa gatggtgaat tggggatata   4800
tgatgagatg ataccaagct atacaatatt tcacaatgat actgaaacat tttccagcct   4860
ttggactgag tgtaagtctg actttaaatc attttttagca gattatgaaa gtgatacgca   4920
acggtatgga aacaatcata gaatggaagg aaagccaaat gctccggaaa acatttttaa   4980
tgtatctatg ataccgtggt caaccttcga tggctttaat ctgaatttgc agaaaggata   5040
tgattatttg attcctattt ttactatggg gaaatattat aaagaagata acaaaattat   5100
acttcctttg gcaattcaag ttcatcacgc agtatgtgac ggattcaca tttgccgttt   5160 tgtaaacgaa ttgcaggaat tgataaatag ttaacttcag gtttgtctgt aactaaaaac   5220
aagtatttaa gcaaaaacat cgtagaaata cggtgttttt tgttacccta agtttaaact   5280 ccttttttgat aatctcatga ccaaaatccc ttaacgtgag ttttcgttcc actgagcgtc   5340 agacccgta gaaaagatca aaggatcttc ttgagatcct ttttttctgc gcgtaatctg   5400
ctgcttgcaa acaaaaaaac caccgctacc agcggtggtt tgtttgccgg atcaagagct   5460
accaactctt tttccgaagg taactggctt cagcagagcg cagataccaa atactgttct   5520
```

```
tctagtgtag ccgtagttag gccaccactt caagaactct gtagcaccgc ctacatacct    5580
cgctctgcta atcctgttac cagtggctgc tgccagtggc gataagtcgt gtcttaccgg    5640
gttggactca agacgatagt taccggataa ggcgcagcgg tcgggctgaa cggggggttc    5700
gtgcacacag cccagcttgg agcgaacgac ctacaccgaa ctgagatacc tacagcgtga    5760
gctatgagaa agcgccacgc ttcccgaagg gagaaaggcg gacaggtatc cggtaagcgg    5820
cagggtcgga acaggagagc gcacgaggga gcttccaggg ggaaacgcct ggtatcttta    5880
tagtcctgtc gggtttcgcc acctctgact tgagcgtcga ttttgtgat gctcgtcagg    5940 ggggcggagc ctatggaaaa acgccagcaa cgcggccttt ttacggttcc tggccttttg    6000
ctggcctttt gctcacatgt tctttcctgc gttatcccct gattctgtgg ataaccgtat    6060
taccgccttt gagtgagctg ataccgctcg ccgcagccga acgaccgagc gcagcgagtc    6120
agtgagcgag gaagcggaag agcgcccaat acgcagggcc ccctgcttcg ggtcattat    6180 agcgatttt tcggtatatc catccttttt cgcacgatat acaggatttt gccaagggt    6240 tcgtgtagac tttccttggt gtatccaacg gcgtcagccg gcaggatag gtgaagtagg    6300 cccacccgcg agcgggtgtt ccttcttcac tgtcccttat tcgcacctgg cggtgctcaa    6360
cgggaatcct gctctgcgag gctggccggc taccgccggc gtaacagatg agggcaagcg    6420
gatggctgat gaaaccaagc caaccaggaa gggcagccca cctatcaagg tgtactgcct    6480
tccagacgaa cgaagagcga ttgaggaaaa ggcggcggcg gccggcatga gcctgtcggc    6540
ctacctgctg gccgtcggcc agggctacaa aatcacgggc gtcgtggact atgagcacgt    6600
ccgcgagctg gcccgcatca atggcgacct gggccgcctg gcggccctgc tgaaactctg    6660
gctcaccgac gacccgcgca cggcgcggtt cggtgatgcc acgatcctcg ccctgctggc    6720
gaagatcgaa gagaagcagg acgagcttgg caaggtcatg atgggcgtgg tccgcccgag    6780
ggcagagcca tgactttttt agccgctaaa acggccgggg ggtgcgcgtg attgccaagc    6840
acgtccccat gcgctccatc aagaagagcg acttcgcgga gctggtgaag tacatcaccg    6900
acgagcaagg caagaccgat cgggccc                                        6927
```

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21

```
tggagtgctg gtggcctgtt                                                  20
```

<210> SEQ ID NO 22
<211> LENGTH: 27
<212> TYPE: DNA
<213> ORGANISM: Artificial sequence
<220> FEATURE:
<223> OTHER INFORMATION: Synthetic

<400> SEQUENCE: 22

```
aaaagctgta ctagtagctg atgccgt                                          27
```

<210> SEQ ID NO 23
<211> LENGTH: 25
<212> TYPE: DNA
<213> ORGANISM: Artificial sequence
<220> FEATURE:
<223> OTHER INFORMATION: Synthetic

<400> SEQUENCE: 23
gagctggtac atatagccat catgc                                              25

<210> SEQ ID NO 24
<211> LENGTH: 27
<212> TYPE: DNA
<213> ORGANISM: Artificial sequence
<220> FEATURE:
<223> OTHER INFORMATION: Synthetic

<400> SEQUENCE: 24
ctgtaccatt tcaagtccta tttgtgc                                            27

<210> SEQ ID NO 25
<211> LENGTH: 23
<212> TYPE: DNA
<213> ORGANISM: Artificial sequence
<220> FEATURE:
<223> OTHER INFORMATION: Synthetic

<400> SEQUENCE: 25
gcgagagttt gatcctggct cag                                                23

<210> SEQ ID NO 26
<211> LENGTH: 22
<212> TYPE: DNA
<213> ORGANISM: Artificial sequence
<220> FEATURE:
<223> OTHER INFORMATION: Synthetic

<400> SEQUENCE: 26
cgcggttacc ttgttacgac tt                                                 22

<210> SEQ ID NO 27
<211> LENGTH: 28
<212> TYPE: DNA
<213> ORGANISM: Artificial sequence
<220> FEATURE:
<223> OTHER INFORMATION: Synthetic

<400> SEQUENCE: 27
cgaaattaga aacttgcgtt cagtaaac                                           28

<210> SEQ ID NO 28
<211> LENGTH: 32
<212> TYPE: DNA
<213> ORGANISM: Artificial sequence
<220> FEATURE:
<223> OTHER INFORMATION: Synthetic

<400> SEQUENCE: 28
attactgtga ctggtttgca ccaccctctt cg                                      32

<210> SEQ ID NO 29
<211> LENGTH: 29
<212> TYPE: DNA
<213> ORGANISM: Artificial sequence
<220> FEATURE:
<223> OTHER INFORMATION: Synthetic

<400> SEQUENCE: 29
aagcggccgc agatagtcat aatagttcc                                          29

<210> SEQ ID NO 30
<211> LENGTH: 29
<212> TYPE: DNA

```
<213> ORGANISM: Artificial sequence
<220> FEATURE:
<223> OTHER INFORMATION: Synthetic

<400> SEQUENCE: 30
ttccatatga ataattccct ccttaaagc                                          29

<210> SEQ ID NO 31
<211> LENGTH: 27
<212> TYPE: DNA
<213> ORGANISM: Artificial sequence
<220> FEATURE:
<223> OTHER INFORMATION: Synthetic

<400> SEQUENCE: 31
gggaattagc catatggaag aaaaagc                                            27

<210> SEQ ID NO 32
<211> LENGTH: 19
<212> TYPE: DNA
<213> ORGANISM: Artificial sequence
<220> FEATURE:
<223> OTHER INFORMATION: Synthetic

<400> SEQUENCE: 32
atttgagctc tggcatggc                                                     19

<210> SEQ ID NO 33
<211> LENGTH: 23
<212> TYPE: DNA
<213> ORGANISM: Artificial sequence
<220> FEATURE:
<223> OTHER INFORMATION: Synthetic

<400> SEQUENCE: 33
caagaaccca tgtgaagtac agg                                                23

<210> SEQ ID NO 34
<211> LENGTH: 23
<212> TYPE: DNA
<213> ORGANISM: Artificial sequence
<220> FEATURE:
<223> OTHER INFORMATION: Synthetic

<400> SEQUENCE: 34
cctgtacttc acatgggttc ttg                                                23

<210> SEQ ID NO 35
<211> LENGTH: 28
<212> TYPE: DNA
<213> ORGANISM: Artificial sequence
<220> FEATURE:
<223> OTHER INFORMATION: Synthetic

<400> SEQUENCE: 35
aggctacttt acaattattg gacaaggc                                           28

<210> SEQ ID NO 36
<211> LENGTH: 28
<212> TYPE: DNA
<213> ORGANISM: Artificial sequence
<220> FEATURE:
<223> OTHER INFORMATION: Synthetic

<400> SEQUENCE: 36
gcccttggat atacacctaa ttttctcc                                           28
```